(12) United States Patent
Orphanos et al.

(10) Patent No.: US 10,874,415 B2
(45) Date of Patent: Dec. 29, 2020

(54) UNITARY ENDOSCOPIC VESSEL HARVESTING DEVICES

(71) Applicant: Saphena Medical, Inc., West Bridgewater, MA (US)

(72) Inventors: Mark J. Orphanos, Foxboro, MA (US); Michael Glennon, Norwell, MA (US)

(73) Assignee: Saphena Medical, Inc., West Bridgewater, MA (US)

( * ) Notice: Subject to any disclaimer, the term of this patent is extended or adjusted under 35 U.S.C. 154(b) by 0 days.

(21) Appl. No.: 16/524,958

(22) Filed: Jul. 29, 2019

(65) Prior Publication Data

US 2019/0343547 A1    Nov. 14, 2019

Related U.S. Application Data

(62) Division of application No. 15/184,153, filed on Jun. 16, 2016, now Pat. No. 10,363,056.

(Continued)

(51) Int. Cl.
*A61B 17/32* (2006.01)
*A61B 17/3205* (2006.01)
(Continued)

(52) U.S. Cl.
CPC .. *A61B 17/320016* (2013.01); *A61B 1/00082* (2013.01); *A61B 1/00087* (2013.01);
(Continued)

(58) Field of Classification Search
CPC ............ A61B 1/00082; A61B 1/00163; A61B 17/320016; A61B 17/00234
(Continued)

(56) References Cited

U.S. PATENT DOCUMENTS 5,373,840 A    12/1994  Knighton
5,556,408 A     9/1996  Farhat
(Continued)

FOREIGN PATENT DOCUMENTS

EP    1570787 B1    9/2005
EP    2364653 A1    9/2011
(Continued)

OTHER PUBLICATIONS

European Search Report issued in European Application No. EP 14773921 dated Feb. 17, 2017.

(Continued)

*Primary Examiner* — Matthew J Kasztejna
(74) *Attorney, Agent, or Firm* — Greenberg Traurig, LLP; Chinh H. Pham; Brian J. Assessor

(57) ABSTRACT

Unitary endoscopic vessel harvesting devices are disclosed. In some embodiments, such devices comprise an elongated body having a proximal end and a distal end; an inflatable, coated or conditioned tip disposed at the distal end of the elongated body; and a cutting unit having a first cutting portion and a second cutting portion, the first cutting portion and the second cutting portion being moveable in a longitudinal direction relative to the elongated body to capture a blood vessel between the first cutting portion and the second cutting portion, and being rotatable relative to one another circumferentially about the tip to cut the captured blood vessel.

11 Claims, 24 Drawing Sheets

Related U.S. Application Data

(60) Provisional application No. 62/180,794, filed on Jun. 17, 2015.

(51) Int. Cl.

| | | |
|---|---|---|
| *A61B 17/12* | (2006.01) | |
| *A61B 1/00* | (2006.01) | |
| *A61B 17/00* | (2006.01) | |
| *A61B 17/34* | (2006.01) | |
| *A61B 18/08* | (2006.01) | |
| *A61B 18/14* | (2006.01) | |
| A61B 17/122 | (2006.01) | |
| A61B 17/3201 | (2006.01) | |
| A61B 18/00 | (2006.01) | |
| A61B 90/00 | (2016.01) | |

(52) U.S. Cl.
CPC .... *A61B 17/00008* (2013.01); *A61B 17/3205* (2013.01); *A61B 17/32053* (2013.01); *A61B 17/3417* (2013.01); *A61B 18/085* (2013.01); *A61B 18/148* (2013.01); A61B 17/122 (2013.01); A61B 17/12013 (2013.01); A61B 17/3201 (2013.01); A61B 18/1445 (2013.01); A61B 90/37 (2016.02); A61B 2017/00349 (2013.01); A61B 2017/00473 (2013.01); A61B 2017/00778 (2013.01); A61B 2017/00907 (2013.01); A61B 2017/00969 (2013.01); A61B 2017/320048 (2013.01); A61B 2017/320064 (2013.01); A61B 2017/3445 (2013.01); A61B 2017/3454 (2013.01); A61B 2018/00196 (2013.01); A61B 2018/00386 (2013.01); A61B 2018/00404 (2013.01); A61B 2018/00589 (2013.01); A61B 2018/00595 (2013.01); A61B 2018/00601 (2013.01); A61B 2018/00607 (2013.01); A61B 2018/00982 (2013.01); A61B 2018/145 (2013.01); A61B 2018/1415 (2013.01); A61B 2018/1475 (2013.01)

(58) Field of Classification Search
USPC .......... 600/114–115, 127, 129; 606/190–200
See application file for complete search history.

(56) References Cited

U.S. PATENT DOCUMENTS

| | | |
|---|---|---|
| 5,591,183 A | 1/1997 | Chin |
| 5,676,636 A | 10/1997 | Chin |
| 5,695,514 A | 12/1997 | Chin |
| 5,728,123 A | 3/1998 | Lemelson et al. |
| 5,772,576 A | 6/1998 | Knighton et al. |
| 5,797,946 A | 8/1998 | Chin |
| 5,810,805 A | 9/1998 | Sutcu et al. |
| 5,823,946 A | 10/1998 | Chin |
| 5,873,889 A | 2/1999 | Chin |
| 5,891,141 A | 4/1999 | Rydell |
| 5,895,353 A | 4/1999 | Lunsford et al. |
| 5,916,233 A | 6/1999 | Chin |
| 5,921,919 A | 7/1999 | Chin et al. |
| 5,941,819 A | 8/1999 | Chin |
| 5,968,065 A | 10/1999 | Chin |
| 5,976,168 A | 11/1999 | Chin |
| 5,980,549 A | 11/1999 | Chin |
| 5,984,937 A | 11/1999 | Morse et al. |
| 5,993,384 A | 11/1999 | Lunsford et al. |
| 6,019,771 A | 2/2000 | Bennett et al. |
| 6,030,406 A | 2/2000 | Davis et al. |
| 6,036,714 A | 3/2000 | Chin |
| 6,042,538 A | 3/2000 | Puskas |
| 6,102,909 A | 8/2000 | Chen et al. |
| 6,162,173 A | 12/2000 | Chin et al. |
| 6,176,825 B1 | 1/2001 | Chin et al. |
| 6,203,557 B1 | 3/2001 | Chin |
| 6,203,559 B1 | 3/2001 | Davis et al. |
| 6,264,670 B1 | 7/2001 | Chin |
| 6,277,137 B1 | 8/2001 | Chin |
| 6,287,304 B1 | 9/2001 | Eggers et al. |
| 6,348,037 B1 | 2/2002 | Chin et al. |
| 6,402,720 B1 | 6/2002 | Miller et al. |
| 6,406,425 B1 | 6/2002 | Chin et al. |
| 6,428,468 B1 | 8/2002 | Knighton et al. |
| 6,428,539 B1 | 8/2002 | Baxter et al. |
| 6,428,556 B1 | 8/2002 | Chin |
| 6,432,044 B1 | 8/2002 | Lunsford et al. |
| 6,471,638 B1 | 10/2002 | Chang et al. |
| 6,506,200 B1 | 1/2003 | Chin |
| 6,569,082 B1 | 5/2003 | Chin |
| 6,607,547 B1 | 8/2003 | Chin |
| 6,673,087 B1 | 1/2004 | Chang et al. |
| 6,702,813 B1 | 3/2004 | Baxter et al. |
| 6,706,052 B1 | 3/2004 | Chin |
| 6,749,609 B1 | 6/2004 | Lunsford et al. |
| 6,752,756 B2 | 6/2004 | Lunsford et al. |
| 6,811,546 B1 | 11/2004 | Callas et al. |
| 6,814,696 B1 | 11/2004 | Chang et al. |
| 6,830,546 B1 | 12/2004 | Chin et al. |
| 6,951,568 B1 | 10/2005 | Chin |
| 6,976,957 B1 | 12/2005 | Chin et al. |
| 6,979,290 B2 | 12/2005 | Mourlas |
| 7,001,404 B1 | 2/2006 | Chin |
| 7,033,357 B2 | 4/2006 | Baxter et al. |
| 7,066,875 B2 | 6/2006 | Knighton et al. |
| 7,214,180 B2 | 5/2007 | Chin |
| 7,264,587 B2 | 9/2007 | Chin |
| 7,276,075 B1 | 10/2007 | Callas et al. |
| 7,326,178 B1 | 2/2008 | Lunsford et al. |
| 7,344,536 B1 | 3/2008 | Lunsford et al. |
| 7,384,423 B1 | 6/2008 | Chin |
| 7,398,781 B1 | 7/2008 | Chin |
| 7,476,198 B1 | 1/2009 | Chin et al. |
| 7,485,092 B1 | 2/2009 | Stewart et al. |
| 7,534,243 B1 | 5/2009 | Chin et al. |
| 7,544,195 B2 | 6/2009 | Lunsford et al. |
| 7,556,633 B2 | 7/2009 | Lindsay |
| 7,645,289 B2 | 1/2010 | Bayer |
| 7,695,470 B1 | 4/2010 | Stewart et al. |
| 7,867,163 B2 | 1/2011 | Chin et al. |
| 7,887,558 B2 | 2/2011 | Lin et al. |
| 7,918,848 B2 | 4/2011 | Lau et al. |
| 7,931,590 B2 | 4/2011 | Willis |
| 7,938,842 B1 | 5/2011 | Chin |
| 7,972,265 B1 | 7/2011 | Chin et al. |
| 7,981,133 B2 | 7/2011 | Chin |
| 8,075,559 B2 | 12/2011 | Stewart et al. |
| 8,083,664 B2 | 12/2011 | Davis |
| 8,197,472 B2 | 6/2012 | Lau et al. |
| 8,241,210 B2 | 8/2012 | Lunsford et al. |
| 8,372,096 B2 | 2/2013 | Kadykowski et al. |
| 8,414,480 B2 | 4/2013 | Kendale et al. |
| 8,460,331 B2 | 6/2013 | Chin |
| 8,623,003 B2 | 1/2014 | Lau et al. |
| 8,657,818 B2 | 2/2014 | Lin |
| 9,498,246 B2 | 11/2016 | Chin et al. |
| 9,730,782 B2 | 8/2017 | Stewart |
| 9,943,328 B2 | 4/2018 | Orphanos |
| 10,363,056 B2 | 7/2019 | Orphanos et al. |
| 2003/0229366 A1 | 12/2003 | Reggie et al. |
| 2004/0133228 A1 | 7/2004 | Bayer |
| 2004/0243167 A1 | 12/2004 | Tanaka et al. |
| 2005/0154262 A1* | 7/2005 | Banik ............... A61B 1/00059 600/179 |
| 2005/0192613 A1 | 9/2005 | Lindsay |
| 2005/0272975 A1* | 12/2005 | McWeeney ........ A61B 1/00071 600/113 |
| 2006/0095056 A1 | 5/2006 | Douglas et al. |
| 2006/0271032 A1 | 11/2006 | Chin et al. |
| 2007/0016183 A1 | 1/2007 | Lee et al. |
| 2008/0208192 A1 | 8/2008 | Kadykowski et al. |
| 2008/0306335 A1 | 12/2008 | Lau et al. |
| 2009/0023986 A1 | 1/2009 | Stewart et al. |
| 2010/0191057 A1 | 7/2010 | Jansen |

(56) References Cited

U.S. PATENT DOCUMENTS

| | | |
|---|---|---|
| 2010/0268175 A1 | 10/2010 | Lunsford et al. |
| 2012/0149983 A1 | 6/2012 | Chin |
| 2012/0232342 A1 | 9/2012 | Reydel |
| 2012/0289957 A1 | 11/2012 | Emmerich |
| 2013/0046138 A1* | 2/2013 | McLawhorn ...... A61B 1/00101 600/104 |
| 2013/0144276 A1* | 6/2013 | Crisostomo ........... A61F 2/2427 606/1 |
| 2013/0797299 | 8/2013 | Chin et al. |
| 2013/0274548 A1 | 10/2013 | Fels et al. |
| 2014/0296847 A1 | 10/2014 | Chin et al. |
| 2014/0378957 A1 | 12/2014 | Orphanos et al. |
| 2015/0141938 A1 | 5/2015 | Pravongviengkham et al. |

FOREIGN PATENT DOCUMENTS

| | | |
|---|---|---|
| JP | 2000-505315 A | 5/2000 |
| JP | 2016-514016 A | 5/2016 |
| WO | 2002/001998 A2 | 1/2002 |
| WO | 2003/013367 A2 | 2/2003 |
| WO | 2004/043530 A1 | 5/2004 |
| WO | 2006/127241 A2 | 11/2006 |
| WO | 2009/148809 A1 | 12/2009 |
| WO | 2011/130399 A1 | 10/2011 |
| WO | 2014/158613 A1 | 10/2014 |
| WO | 2015/191816 A1 | 12/2015 |

OTHER PUBLICATIONS

Extended European Search Report issued in European Application No. 16163921.6 dated Sep. 19, 2016.
Extended European Search Report for corresponding European Patent Application No. 14773921, dated Feb. 17, 2017.
Extended European Search Report for European Application No. 16812436.0 dated Apr. 17, 2019.
International Search Report issued in International Application No. PCT/US2014/018737 dated Jun. 18, 2014.
International Search Report issued in International Application No. PCT/US2015/035266 dated Sep. 11, 2015.
International Search Report issued in International Application No. PCT/US2016/037873 dated Sep. 8, 2016.
Office Action in U.S. Appl. No. 14/303,970 dated Jul. 13, 2016.
Office Action for corresponding Japanese Patent Application No. 2016-500439, dated Aug. 22, 2017.
Partial Supplemental European Search Report issued in European Application No. 14773921.3 dated Nov. 10, 2016.

* cited by examiner

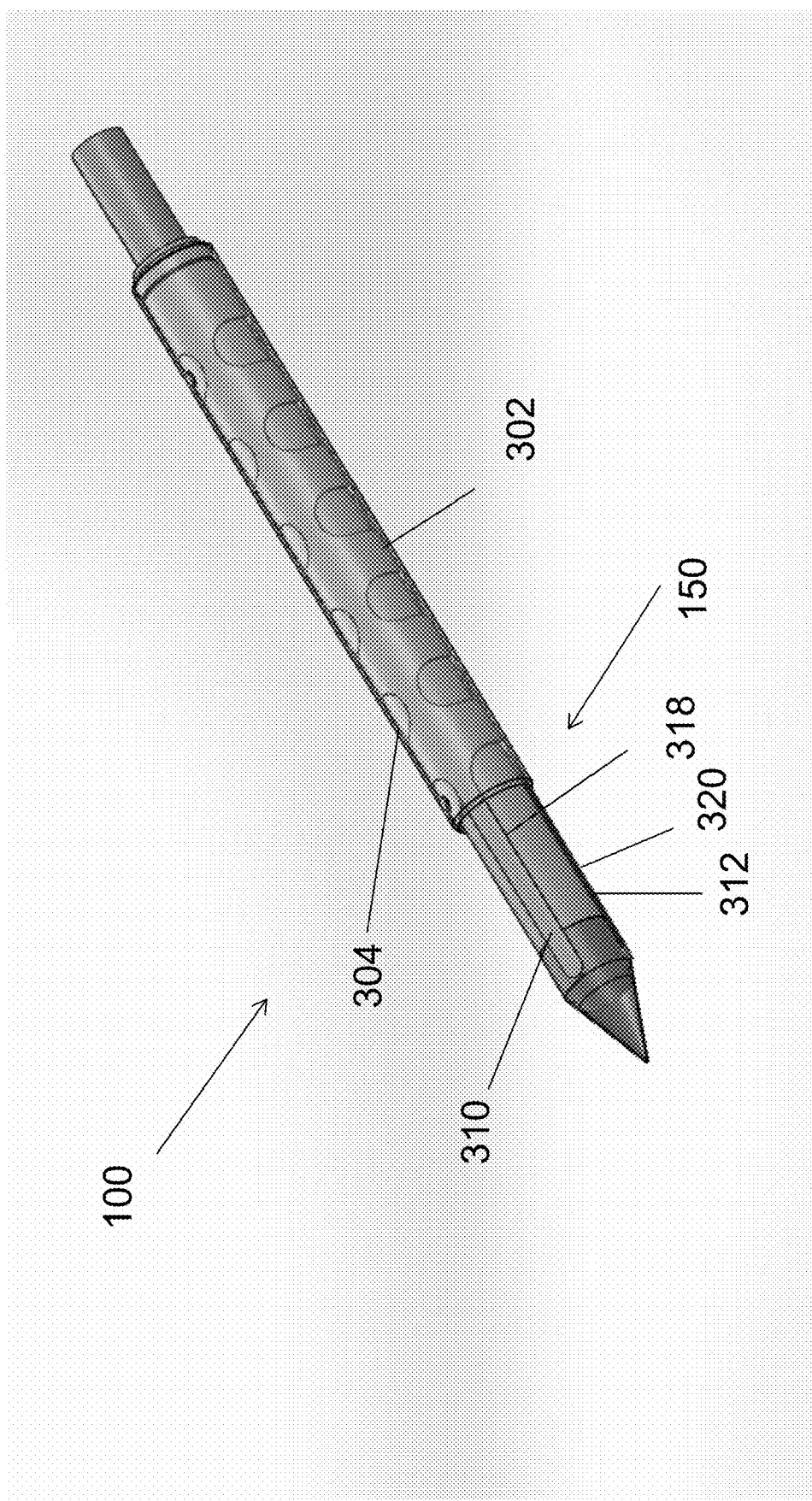

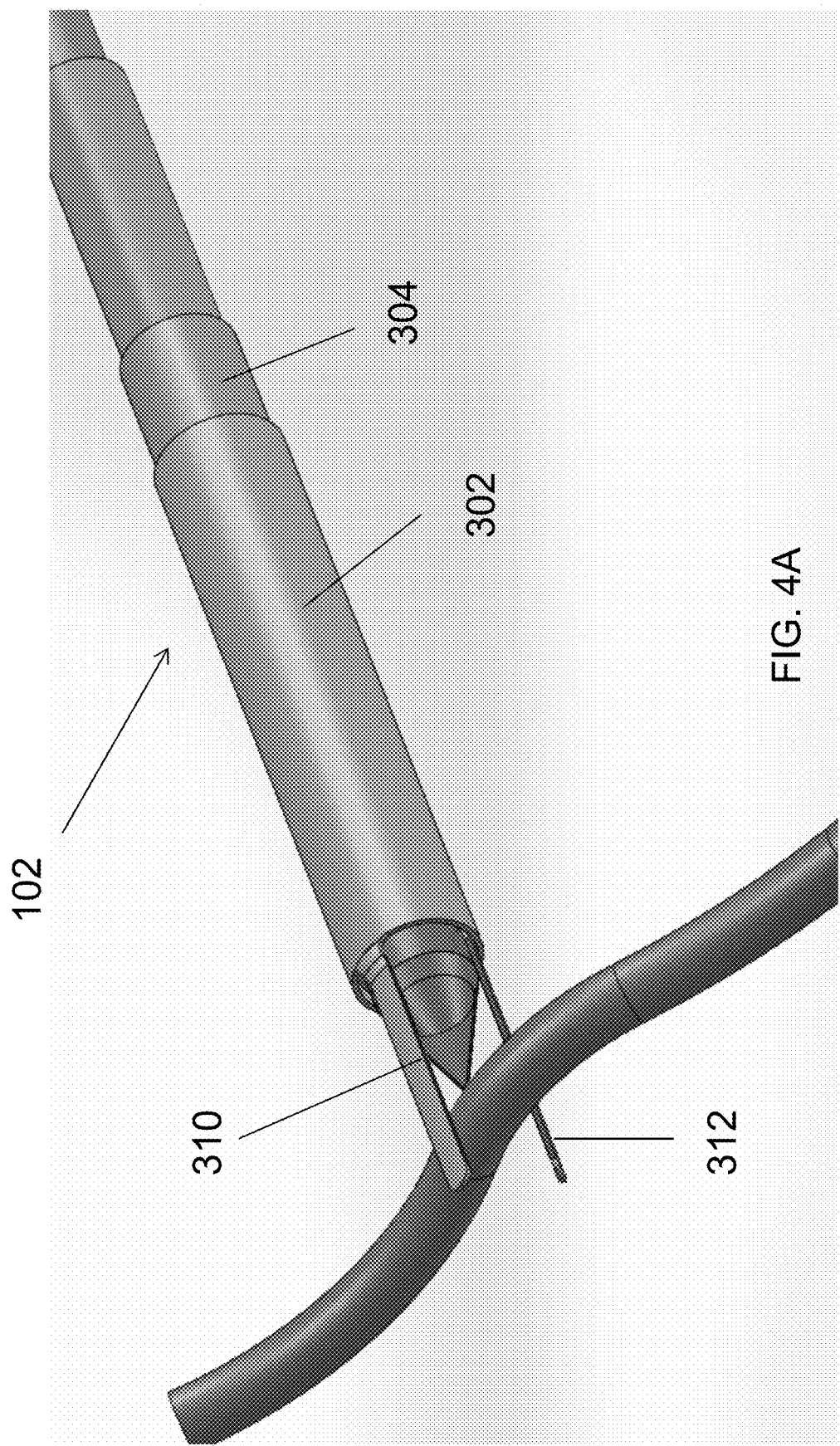

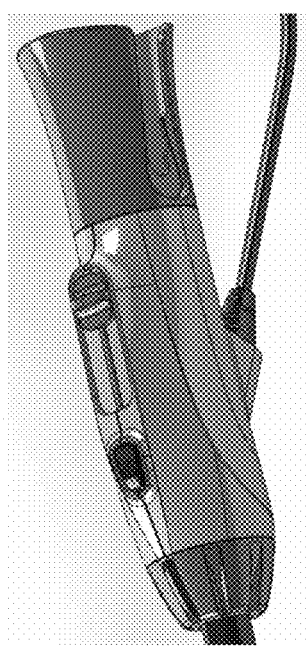
FIG. 6B
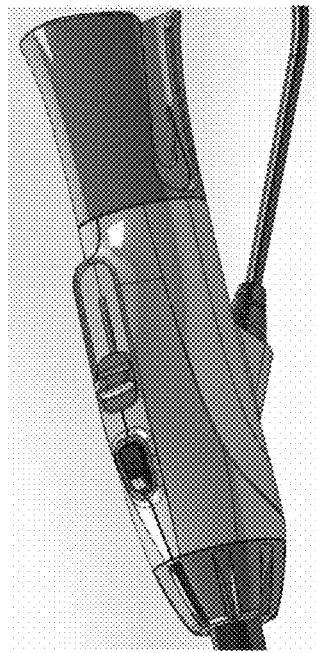
FIG. 6D
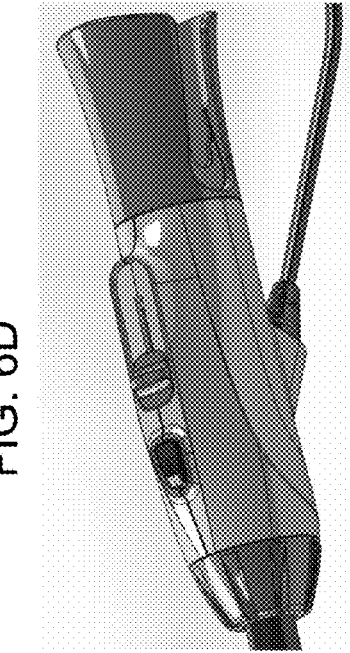
FIG. 6F
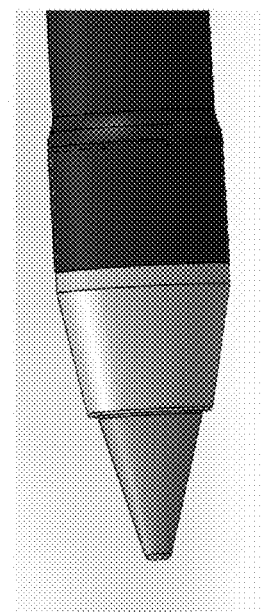
FIG. 6A
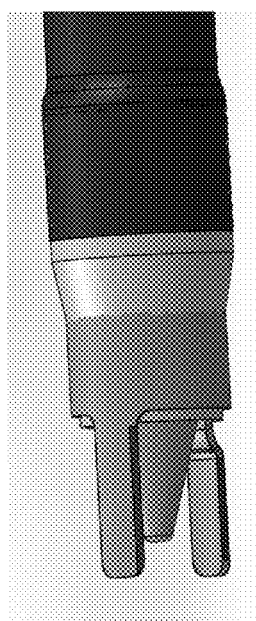
FIG. 6C
FIG. 6E

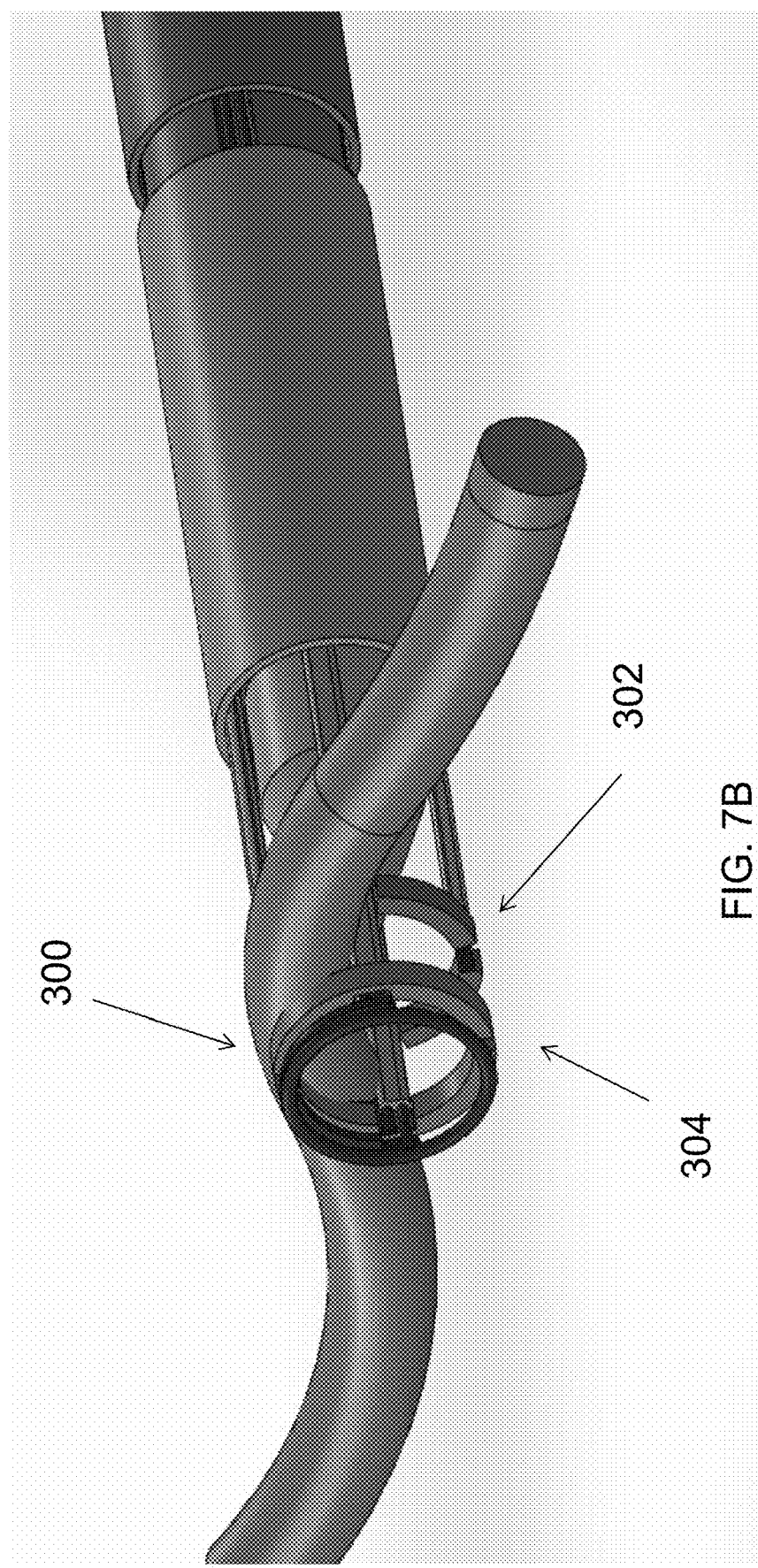

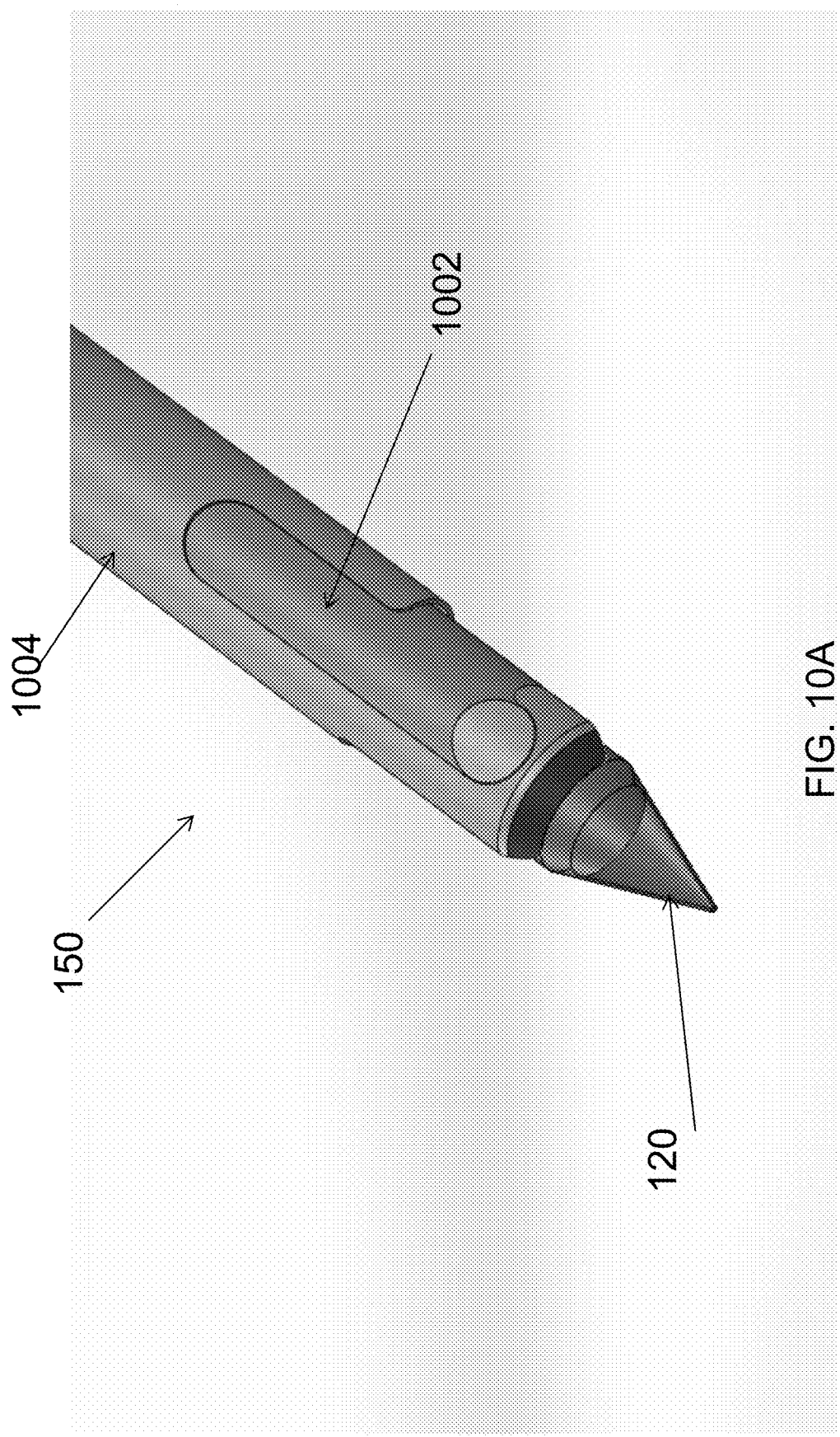

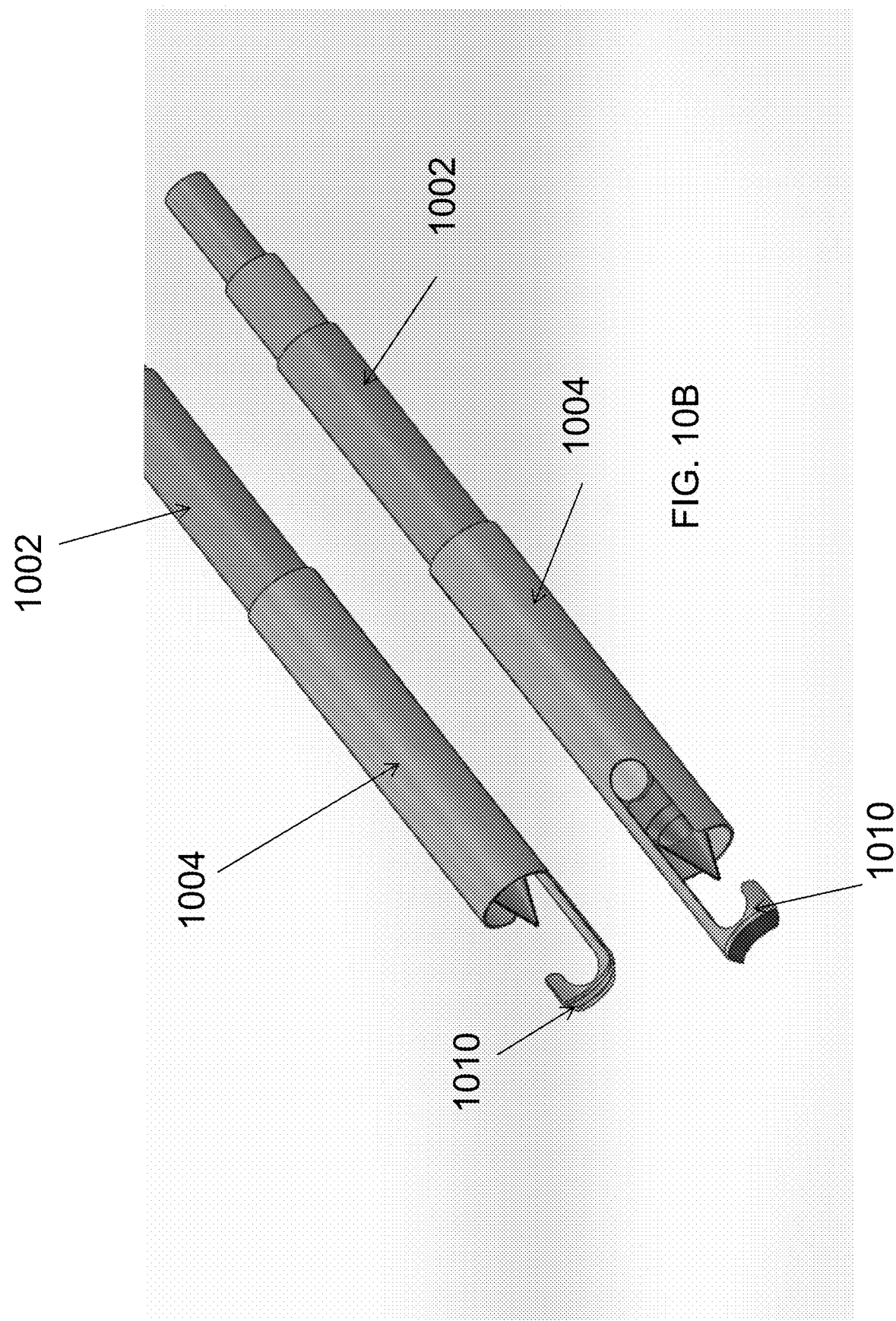

UNITARY ENDOSCOPIC VESSEL HARVESTING DEVICES

RELATED APPLICATION

This application is a divisional application of U.S. application Ser. No. 15/184,153, filed Jun. 16, 2016, which claims priority to and the benefit of U.S. Provisional Application No. 61/180,794, filed Jun. 17, 2015, each of which are incorporated herein by reference in their entireties.

TECHNICAL FIELD

The presently disclosed embodiments relate to endoscopic cannulas and methods of their use.

BACKGROUND

Vessel harvesting is a surgical technique that is commonly used in conjunction with coronary artery bypass surgery. During a bypass surgery, blood is rerouted to bypass blocked arteries to restore and improve blood flow and oxygen to the heart. The blood may be rerouted using a bypass graft, where one end of the by-pass graft is attached to a blood source upstream of the blocked area and the other end is attached downstream of the blocked area, creating a "conduit" channel or new blood flow connection bypassing the blocked area. Commonly, a surgeon will remove or "harvest" healthy blood vessels from another part of the body to create the bypass graft. The success of coronary artery bypass graft surgery may be influenced by the quality of the conduit and how it is handled or treated during the vessel harvest and preparation steps prior to grafting.

Vessel harvesting methods involve selecting a vessel, traditionally, the great saphenous vein in the leg or the radial artery in the arm to be used as a bypass conduit sealing off and cutting smaller blood vessels that branch off the main vessel conduit and harvesting the main conduit from the body. This practice does not harm the remaining blood vessel network, which heals and maintains sufficient blood flow to the extremities, allowing the patient to return to normal function without noticeable effects.

Minimally invasive technique for vessel harvesting is known as endoscopic vessel harvesting, a procedure that requires only small incisions. While the endoscopic vessel harvesting procedure is an improvement over a traditional "open" procedure that required a single, long incision from groin to ankle, the endoscopic procedure is still cumbersome and difficult. In particular, current endoscopic harvesting systems require multiple tools, which increases the potential for injury to the bypass conduit as well as increases the duration of the procedure. Accordingly, improvements in systems and methods for endoscopic vessel harvesting are still needed.

SUMMARY

Unitary endoscopic vessel harvesting devices are disclosed. In an embodiment of the present disclosure, such devices comprise an elongated body having a proximal end and a distal end, an inflatable tip disposed at the distal end of the elongated body; and a cutting unit having a first cutting portion and a second cutting portion, the first cutting portion and the second cutting portion being moveable in a longitudinal direction relative to the elongated body to capture a blood vessel between the first cutting portion and the second cutting portion, and being rotatable relative to one another circumferentially about the tip to cut the captured blood vessel.

In some embodiments, the inflatable tip has an inner cavity in communication with one or more lumens and into which an endoscope is advanced for endoscopic viewing of a harvesting procedure performed by the device. The inflatable tip has a rigid, conical shape when the inflatable tip is fully inflated. The inflatable tip is optically clear so as not to interfere with the endoscopic viewing, and the inflatable tip is comprised of a material sufficient to maintain the conical shape through a vessel dissection. In some embodiments, a wall of the inflatable tip drapes tautly over the endoscope without distorting the endoscopic viewing when the inflatable tip is uninflated.

In some embodiments, such devices comprise an elongated body having a proximal end and a distal end, a conditioned tip disposed at the distal end of the elongated body; and a cutting unit having a first cutting portion and a second cutting portion, the first cutting portion and the second cutting portion being moveable in a longitudinal direction relative to the elongated body to capture a blood vessel between the first cutting portion and the second cutting portion, and being rotatable relative to one another circumferentially about the tip to cut the captured blood vessel. In some embodiments the conditioned tip further comprises a conditioned surface which is conditioned through mechanical polishing techniques or through chemical polishing techniques. In some embodiments the mechanical polishing techniques comprise buffing and the chemical polishing techniques comprise vapor polishing.

In some embodiments, such devices comprise an elongated body having a proximal end and a distal end, a coated tip disposed at the distal end of the elongated body; and a cutting unit having a first cutting portion and a second cutting portion, the first cutting portion and the second cutting portion being moveable in a longitudinal direction relative to the elongated body to capture a blood vessel between the first cutting portion and the second cutting portion, and being rotatable relative to one another circumferentially about the tip to cut the captured blood vessel. In some embodiments, the coated tip further comprises a coating on a surface of the coated tip, the coating providing increased surface tension and lubricity to the coated tip. The coating may be selected from one of paralene, polytetrafluoroethylene, fluorinated ethylene propylene, silicon or tethered liquid perfluorocarbon. In further embodiments, the coating may be applied to an inflatable tip or a conditioned tip.

In some embodiments, the present devices comprise an elongated body having a proximal end and a distal end and an inflatable tip disposed at the distal end of the elongated body, wherein the inflatable tip has a conical shape when the inflatable tip is fully inflated. The device may further include a cutting unit having a first cutting portion and a second cutting portion, the first cutting portion and the second cutting portion being moveable in a longitudinal direction relative to the elongated body from a retracted position substantially proximally of the tip to an extended position over the tip to capture a blood vessel between the first cutting portion and the second cutting portion, and being rotatable relative to one another circumferentially about the tip to cut the captured blood vessel.

BRIEF DESCRIPTION OF DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1D shows the inflatable balloon fully inflated, and FIG. 1E shows the inflatable balloon in an uninflated state.

FIG. 3A, FIG. 3B and FIG. 3C illustrate an embodiment of a cutting unit of an endoscopic cannula of the present disclosure.

FIGS. 4A-4D illustrates an embodiment of a cutting unit of an endoscopic cannula of the present disclosure.

FIGS. 6A-6F illustrate an embodiment of an endoscopic cannula of the present disclosure in operation being controlled by the control handle of FIG. 5.

FIGS. 7A-7B illustrate an embodiment of a cutting unit of an endoscopic cannula of the present disclosure.

FIG. 10A and FIG. 10B illustrate an embodiment of a cutting unit of an endoscopic cannula of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure provides a unitary device for endoscopic vessel harvesting. Present systems for endoscopic vessel harvesting contain multiple components. Typically, an endoscopic dissection device is used to isolate the main vessel from the surrounding connective tissue by dissecting the main vessel from surrounding connective tissue. An endoscopic cannula is then used to introduce yet another device, an endoscopic tributary sealing instrument, to seal and sever side branches. Once the side branches are sealed, yet another device is used to harvest a section of the main vessel to be used as a bypass graft. The unitary devices of the present disclosure combine the dissection function, the tributary sealing and severing function, and, optionally, main vessel sealing and severing function, which can result in decreased vessel manipulation and improvement in ease of the procedure. The devices of the present disclosure may also be used to extract the sealed and severed main vessel from the patient.

Decreased vessel manipulation may decrease the potential for injury to the graft. Repeated vessel contact with multiple passes of harvesting instrumentation increases potential vessel injury. A unitary device such as the device of the present disclosure may dissect, i.e., separate the main vessel, from surrounding tissue, cauterize and transect the tributaries and the main vessel as the device is advanced, and the vessel may be harvested with a single passage of the device, rather than multiple device insertions and retractions. Such a device with a decreased diameter may be used for dissection as well as tributary ligation; graft trauma should be decreased. The relative smaller diameter of the present device can also facilitate harvesting of more tortuous vessels; for example, the internal mammary artery.

Figure 1A:
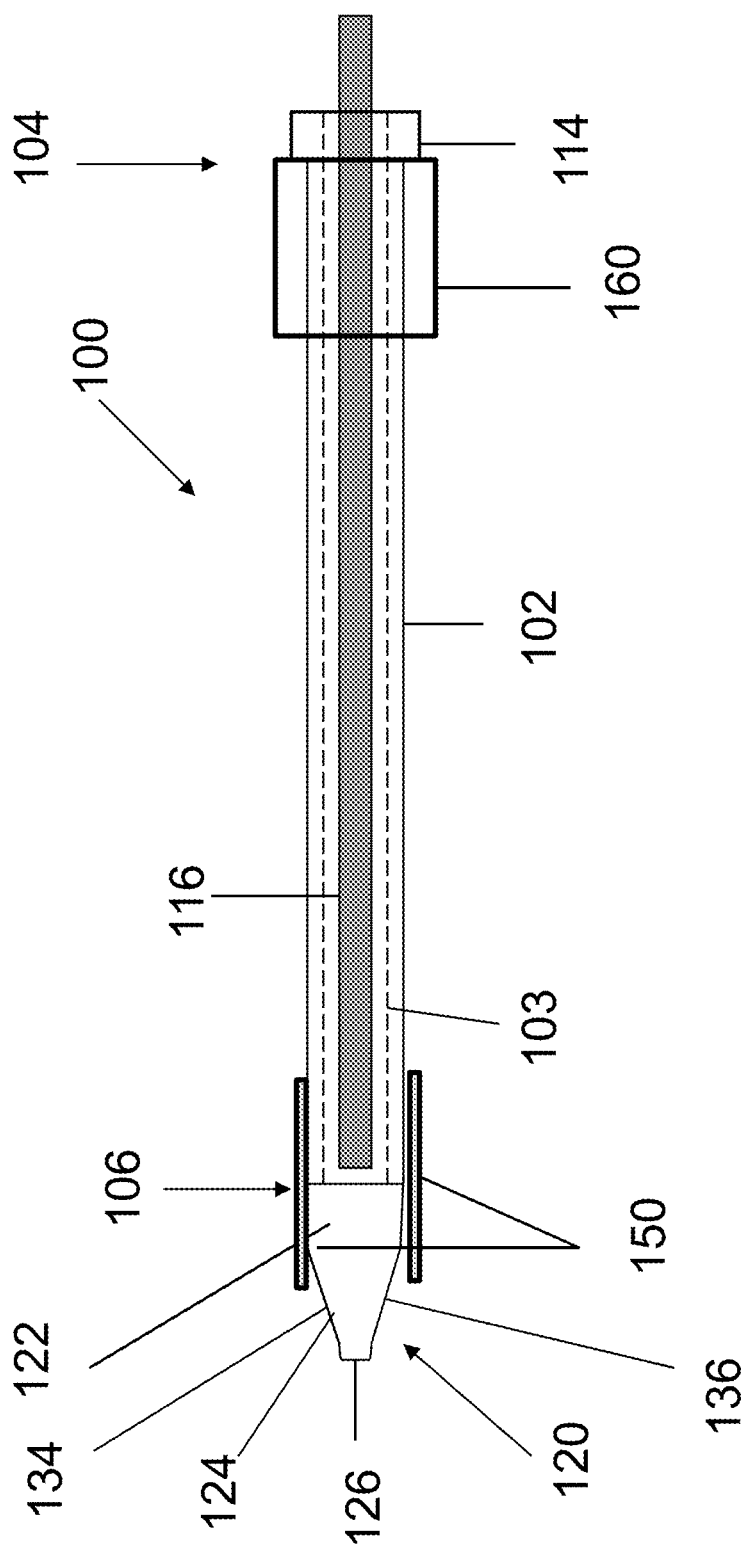
FIG. 1A illustrates a side view of an embodiment of an endoscopic cannula of the present disclosure.

Referring to FIG. 1A, an endoscopic cannula 100 of the present disclosure includes an elongated body 102 having a proximal end 104 and a distal end 106, terminating with a dissection tip 120. The cannula 100 further includes an cutting unit 150 disposed about the distal end 106 for sealing and cutting a blood vessel and a control handle 160 for controlling the cutting unit 150.

In some embodiments, the elongated body 102 is configured for passing extravascularly through an entry incision to a vessel harvesting site. To aid in navigating the elongated body 102 to a site of harvesting, the elongated body 102 may be sufficiently rigid axially along its length. To provide the elongated body 102 with such characteristic, in an embodiment, the elongated body 102 may be made from a biocompatible material, such as, plastic material, elastomeric material, metallic material, shape memory material, composite material or any other materials that has the desired characteristics. To the extent desired, the elongated body 102 may be provided with some flexibility to move radially or laterally from side to side depending on the application.

In some embodiments, the elongated body 102 of the cannula 100 may be solid. In other embodiments, the endoscopic cannula 100 may include one or more lumen with lumen that accommodate advancing instruments or materials therethrough. In some embodiments, the endoscopic cannula 100 may include an endoscopic lumen 103 through which an endoscope 116 may be advanced for visualizing procedures performed using the cannula 100. The endoscopic cannula 100 may include an adapter 114 at the proximal end 104 for advancing the endoscope 116 into the endoscopic cannula 100. Additional lumens of the cannula 100 are described below.

In some embodiments, the endoscopic cannula 100 may include a dissection tip 120 disposed at or about the distal end 106 of the endoscopic cannula 100. The viewing tip of the endoscope may be positioned inside the dissection tip 120. In some embodiments, the dissection tip 120 may include an inner cavity in fluid communication with the endoscopic lumen 103 to enable the endoscope 116 to be advanced into the dissection tip 120. In some embodiments, a chip-on-a-tip type of an endoscope may be integrated inside the dissection tip 120.

The dissection tip 120 may also be transparent to allow for endoscopic viewing through the dissection tip 120 of the procedures performed using the cannula 100. The dissection tip 120 in some embodiments, may be provided with any shape as long as it facilitates endoscopic viewing therethrough, and allows for necessary control during tissue dissecting, i.e. separation. In some embodiments, the dissection tip may be generally conical. In some embodiments the dissection tip 120 may be treated in order to increase optical clarity and to further facilitate endoscopic viewing. In some embodiments the treated dissection tip 120 may have at least one conditioned surface 134 (FIG. 1A). The conditioned surface 134 may be conditioned through mechanical polishing techniques and/or through chemical polishing techniques that will smooth out surface defects on the dissection tip 120. The mechanical polishing techniques may comprise buffing, and the chemical polishing techniques may comprise vapor polishing. In some embodiments, the dissection tip 120 may have at least one coated surface 136 (FIG. 1A). The coated surface 136 will have a coating that can be combined with a balloon or any inflatable tip 130 (FIG. 1D) or a conditioned surface 134. The coating may be configured to increase the surface tension of the coated surface 136 to provide greater resistance to fluids and tissue to remain on the coated surface 136 of the dissection tip 120. In some embodiments, the coating may increase the lubricity of the dissection tip 120, which will not only resist fluids and tissue from remaining on the coated surface 136, but may also provide for reduced dissection loads by reducing friction during the procedure. The coating may be a hydrophobic and/or oleophobic material. In some embodiments the coating is applied in very thin layers, and in preferred embodiments the coating will be less than 0.001" in thickness. In some embodiments, the coating may be applied to the entire device 100 to increase lubricity of the entire device 100. The coating may be selected from one of paralene, polytetrafluoroethylene, fluorinated ethylene propylene, silicon or tethered liquid perfluorocarbon. The coating can be applied with all available manufacturing techniques. The coating can be applied by dipping, spraying, vapor depositing or wiping the coating on the dissection tip 120. The coating can be applied at the component manufacturer level, the assembly manufacturer level, or bedside by the physician. The coating can be applied once, or it can be applied for the life of the device 100, or the coating can be applied by frequent re-application during any procedure. In some embodiments the coating can be dry, and in other embodiments it can be wet.

In some embodiments, the dissection tip 120 may include a generally flat shoulder 122, and a tapered section 124 which terminates in blunt end 126 for atraumatic separation of a vessel segment, being harvested from surrounding tissue, while minimizing or preventing tearing or puncturing of nearby vessels or tissue as the endoscopic cannula 100 is navigated along the vessel segment. Although illustrated as being blunt, it should of course be understood that, to the extent desired, the end 126 of the dissection tip 120 may be made relatively pointed to enhance advancement of the cannula 100.

Figure 1C:
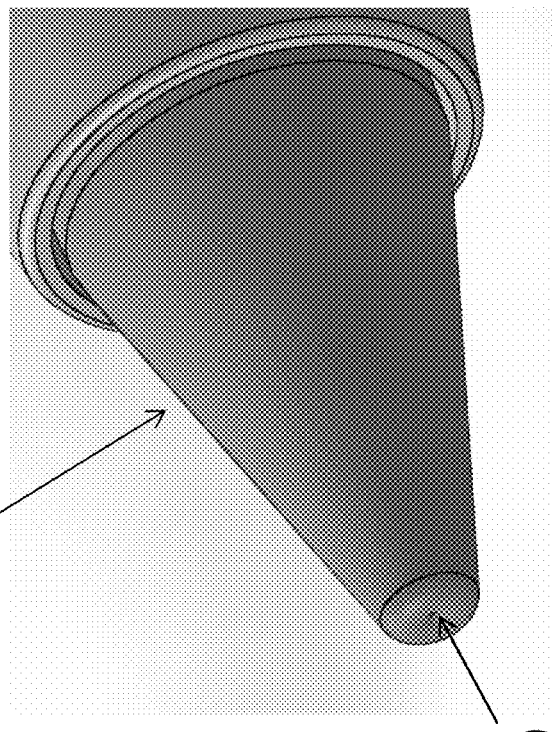
FIG. 1B and FIG. 1C illustrate an embodiment of a dissection tip of the present disclosure having an indent at the distal tip.
Figure 1B:
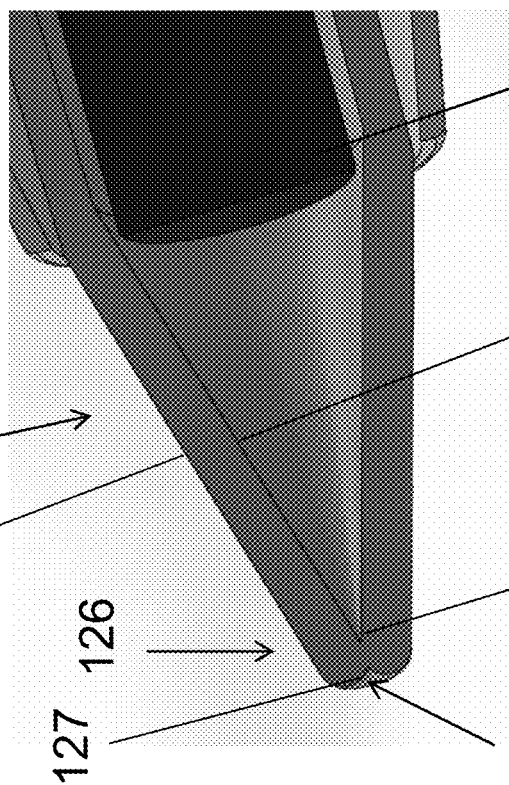

In reference to FIG. 1B and FIG. 1C, in some embodiments, the dissection tip 120 may be cone shaped, and may be shaped at its distal end in a manner so as to minimize the negative effects of visual distortion or blinding at the center of the endoscopic view field when viewing through an endoscope inserted into the cannula 100, with a light source and camera system. Internal surface 121 of the dissection tip 120 may be tapered, with a relatively constant slope toward the distal end 126 of the dissection tip 120, terminating at an internal apex 123, which may be a sharp point, as shown in FIG. 1C. External surface 125 of the dissection tip 120 may also be tapered with a constant slope toward the distal end 126 of the dissection tip 120; however, at the distal end 126, a relatively rounded, blunt end may be formed to minimize tissue damage during dissection. As illustrated, at the distal end, the external surface 125 of the dissection tip 120 may be folded back on itself in a proximal direction to then terminate at an external apex 127, maintaining the blunt exterior surface and forming an indent 129 in the distal end of the dissection tip 120. Both the internal apex 123 and the external apex 127 may be collinear with the central longitudinal axis of the cannula 100 and, thus, in some embodiments, the endoscope 116. In other words, the centers of the internal apex 123 and the external apex 127 are located on the central longitudinal axis of the cannula 100. By providing an apex on each of the internal surface 121 and the external surface 125 of the dissection tip 120 that are also collinear with the axis of the endoscope 116, those surfaces perpendicular to the light path (which is parallel to the endoscope axis) may be eliminated, which then may eliminate light refraction from the perpendicular surface back into the camera and, thus, may minimize or eliminate the visual distortion or blinding when viewing through the endoscope 116 with a light source and camera system.

To reduce likelihood of trauma during the dissection process, in some embodiments, the dissection tip 120 may be radially pliable, flexible or deformable so that the dissection tip may deflect slightly under exertion of force applied to the dissection tip 120. In some embodiments, the dissection tip 120 is radially compressible so that the walls of the dissection tip 120 can deform under exertion of force normal to the tip surface. To that end, the dissection tip 120 may be formed from thin wall plastic material to enable the dissection tip to flex under load. Suitable materials include, but are not limited to, polycarbonate, polyethylene terephthalate glycol-modified (PETG), polyethylene terephthalate (PET) and other materials that provide enough optical clarity while allowing the dissection tip to flex under load. At the same time, the dissection tip 120 may be provided with sufficient column strength in axial or longitudinal direction to allow dissection of the vessel from the surrounding connective tissue.

Figure 2A:
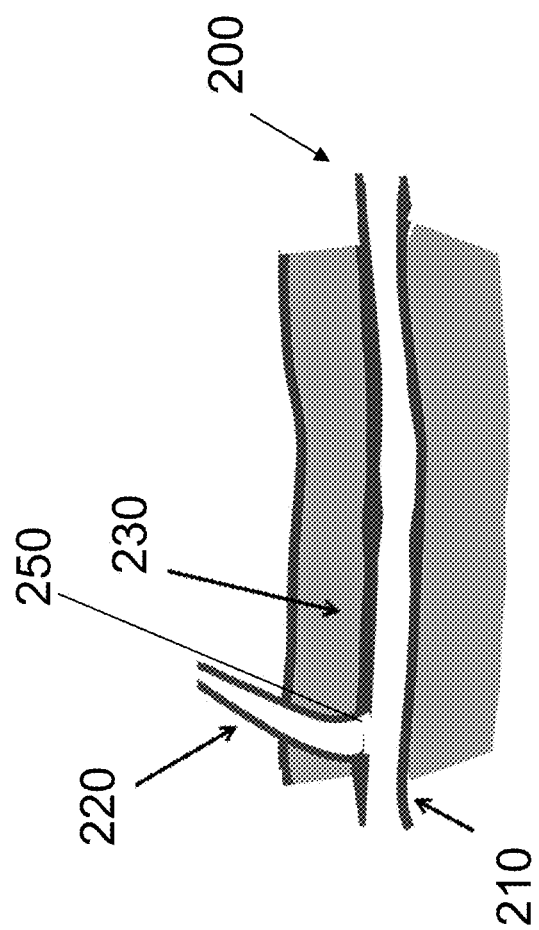
FIGS. 2A-2C illustrate a dissection procedure using an endoscopic cannula of the present disclosure.
Figure 2B:
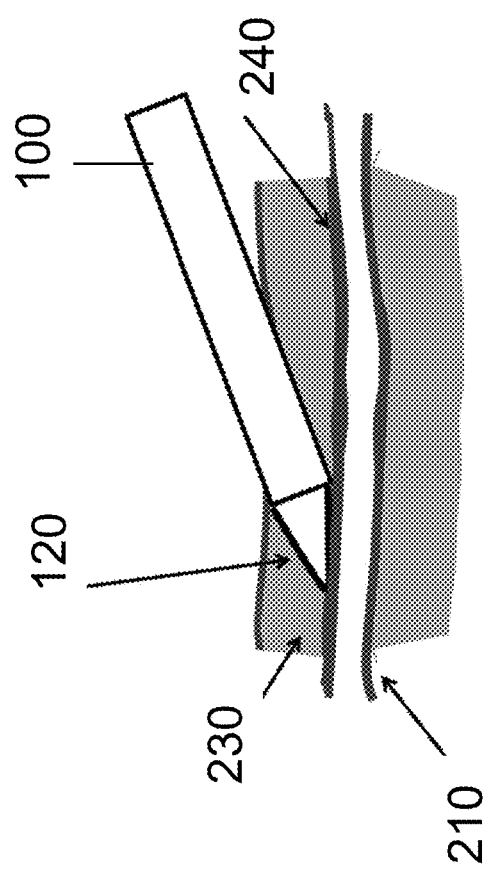
Figure 2C:
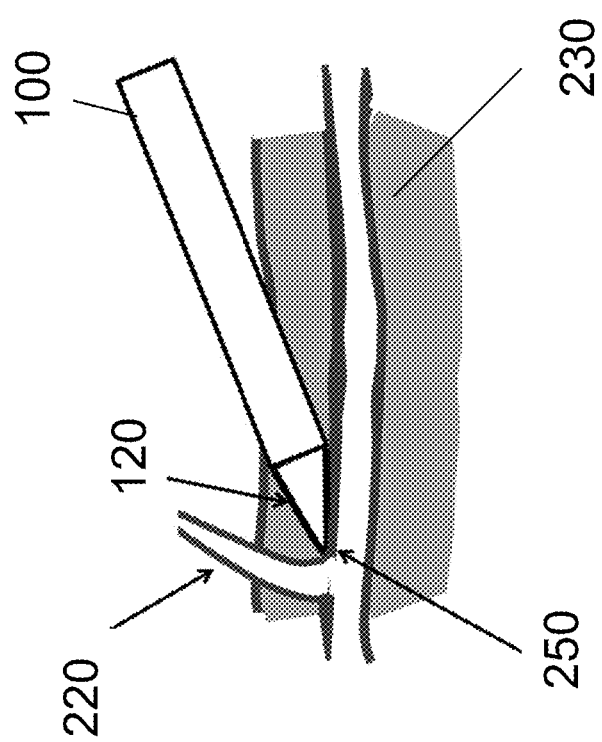

In reference to FIGS. 2A-2C, blood vessels used in bypass grafting (e.g. greater saphenous vein or radial artery), lie in the subcutaneous space, beneath the surface of the skin. The vessel 200 is composed of a main trunk 210, and branch vessels 220 that emanate from the vessel trunk 210, as shown in FIG. 2A. The vessel 200 and its branches 210 are encased in subcutaneous fatty connective tissue 230, and need to be dissected free of the surrounding subcutaneous fatty connective tissue 230 before the main vessel 200 may be harvested. The subcutaneous fatty connective tissue 230 is softer than skin, muscle, fascia or other connective tissues. Although adherent to the vessel 200, the subcutaneous fatty connective tissue 230 forms an interface 240 with the vessel 200 that may be cleanly dissected; that is, there is a natural dissection plane between the outer layer of the vessel 200 (the adventitia), and the surrounding subcutaneous fatty connective tissue 230.

FIG. 2B illustrates dissection of the main trunk 210 of the vessel 200 with the dissection tip 120 along the natural dissection plane, with the dissection tip 120 advanced along the adventitial surface of the vessel 200. Isolation of the vessel 200 from surrounding subcutaneous fatty connective tissue 230 along this plane, typically, does not require high dissection forces. In some embodiments, the dissection tip may 120 be provided with sufficient column strength to dissect the vessel 200 from the surrounding subcutaneous fatty connective tissue 230 along the natural dissection plane between them.

On the other hand, as is illustrated in FIG. 2C, as the dissection tip 120 approaches a branch vessel 220, the dissection tip 120 may catch the branch vessel 220 at a junction 250 between the branch vessel 220 and the main vessel 200. Application of excessive force with the dissection tip 220 may avulse the branch vessel and sever it from the trunk vessel, or may otherwise cause damage to the main vessel 200. To that end, in some embodiments, the dissection tip 120 is provided with sufficient column strength to dissect the vessel 200 from the surrounding tissue 230 along the natural dissection plane between them, while being sufficiently pliable to deform or deflect from the branch vessel 220 with the application of increased force, to decrease the potential of trauma to the graft vessel during dissection around branch vessels. It should of course be understood that the rigidity of the dissection tip 120 may be varied from fully flexible to semi-rigid to rigid, in accordance with requirements of the procedure.

Figure 1D:
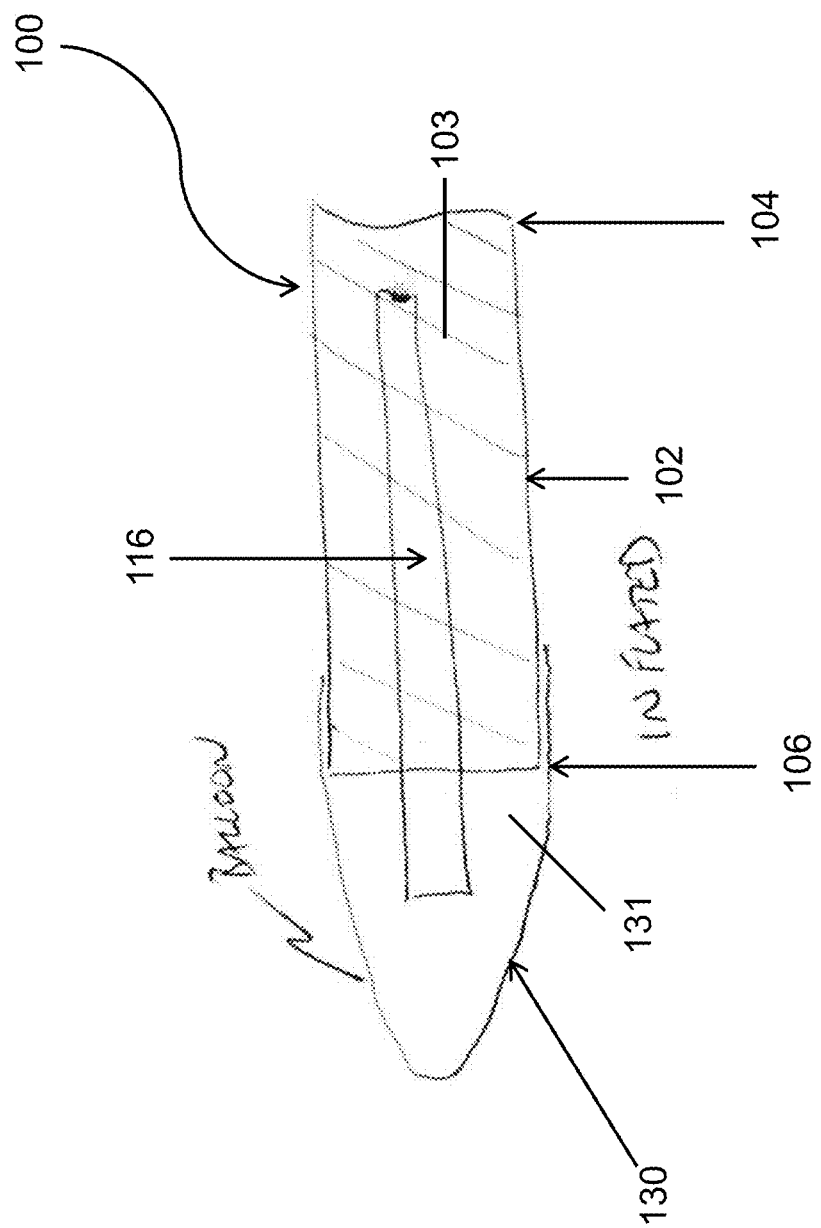
FIG. 1D and FIG. 1E illustrate an alternative embodiment of an endoscopic cannula having a dissection tip comprised of an inflatable balloon at the distal tip.
Figure 1E:
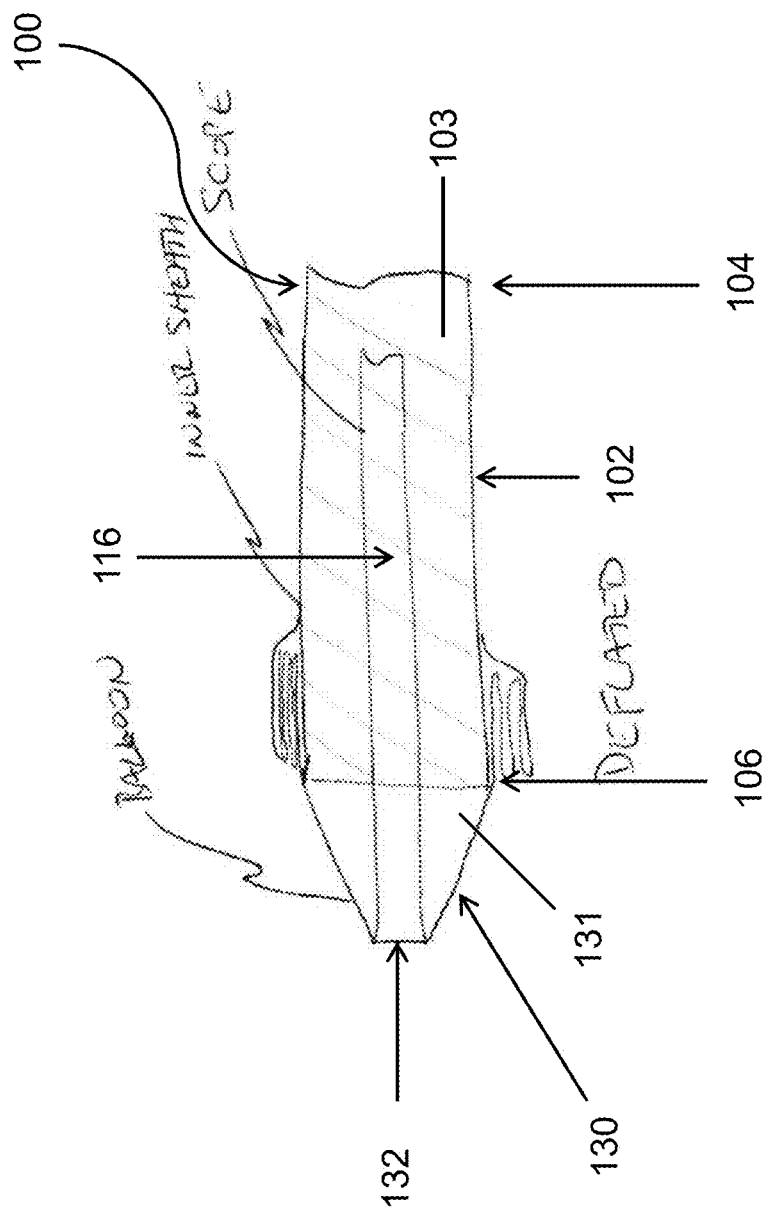

In reference to FIG. 1D and FIG. 1E, the dissection tip 120 may be an inflatable tip 130 disposed at the distal end 106 of the elongated body 102. When inflated, the inflatable tip 130 takes the shape of a dissection cone. The inflatable tip 130 has an inner cavity 131 in communication with one or more lumens 103 and into which an endoscope 116 is advanced for endoscopic viewing of a harvesting procedure performed by the device 100. The endoscope 116 will extend out beyond the end of the lumen 103, and the inflatable tip 130 may be secured and sealed to the outside diameter of the elongated body 102 through normal techniques, such as adhesive or thermal bonding. The inflatable tip 130 is configured to be optically clear so as not to interfere with the endoscopic viewing, and may be deflated to improve optical clarity and allow for performance of endoscopic procedures such as cauterization. To that end, the inflatable tip 130 may be comprised of any material sufficient to handle the inflation pressures needed to support the cone shape through dissection. The inflatable tip 130 may be inflated or deflated by adding or removing a fluid from the inflatable tip 130, a process that is reversible and repeatable and may be done with a syringe or any device capable of injecting or removing the fluid from the tip such as a bladder contained inside the handle of the device 100. The inflation fluid can be a gas, such as, for example, air, or a liquid, such as, for example, saline. When the inflatable tip 130 is deflated as pictured in FIG. 1E, a wall 132 of the deflated inflatable tip 130 may drape tautly over the endoscope 116 without distorting the endoscopic viewing. The wall 132, as draped over the endoscope 116, would not allow for much fluid or tissue build up and would allow more of the clarity of the endoscope 116 camera (not pictured) to be seen without distortion. Furthermore, anything that is on the surface of the wall 132 is proximal to the focal length of the endoscope 116 camera and does not greatly affect the image.

The inflatable tip 130 may be a balloon which, when inflated as pictured in FIG. 1D, takes on the shape of a traditional dissection cone and therefore has a sufficiently rigid, conical shape. There are many types of balloon materials that can be used to fabricate the balloon for the inflatable tip 130. Depending upon the balloon material used, the inflatable tip 130 thickness may change to achieve the needed strength. Consequently, balloon materials requiring larger thicknesses may reduce the optical characteristics and require additional treatments to assist with the optical characteristics. Balloon materials may be, for example, polyurethane, polyethylene terephthalate, nylon, or silicone, and may range in thicknesses from 0.0005" to 0.030". In additional embodiments, the balloon materials that comprise the inflatable tip 130 may be coated to improve optical clarity with a hydrophobic and/or oleophobic material. The coating would increase the surface tension of the balloon and allow it to resist fluids and tissue sticking to or remaining on the cone, which would improve overall visibility. In preferred embodiments the coating would be applied in very thin layers.

The cannula 100 may further include one or more end-effectors for cauterizing or sealing and cutting a blood vessel, either a branch vessel or the main vessel.

In reference to FIG. 3A, in some embodiments, the cutting unit 150 of the cannula 100 may include a first cutting member 302 and a second cutting member 304, each having a cutting portion 310, 312 extending from their respective distal ends.

Figure 3B:
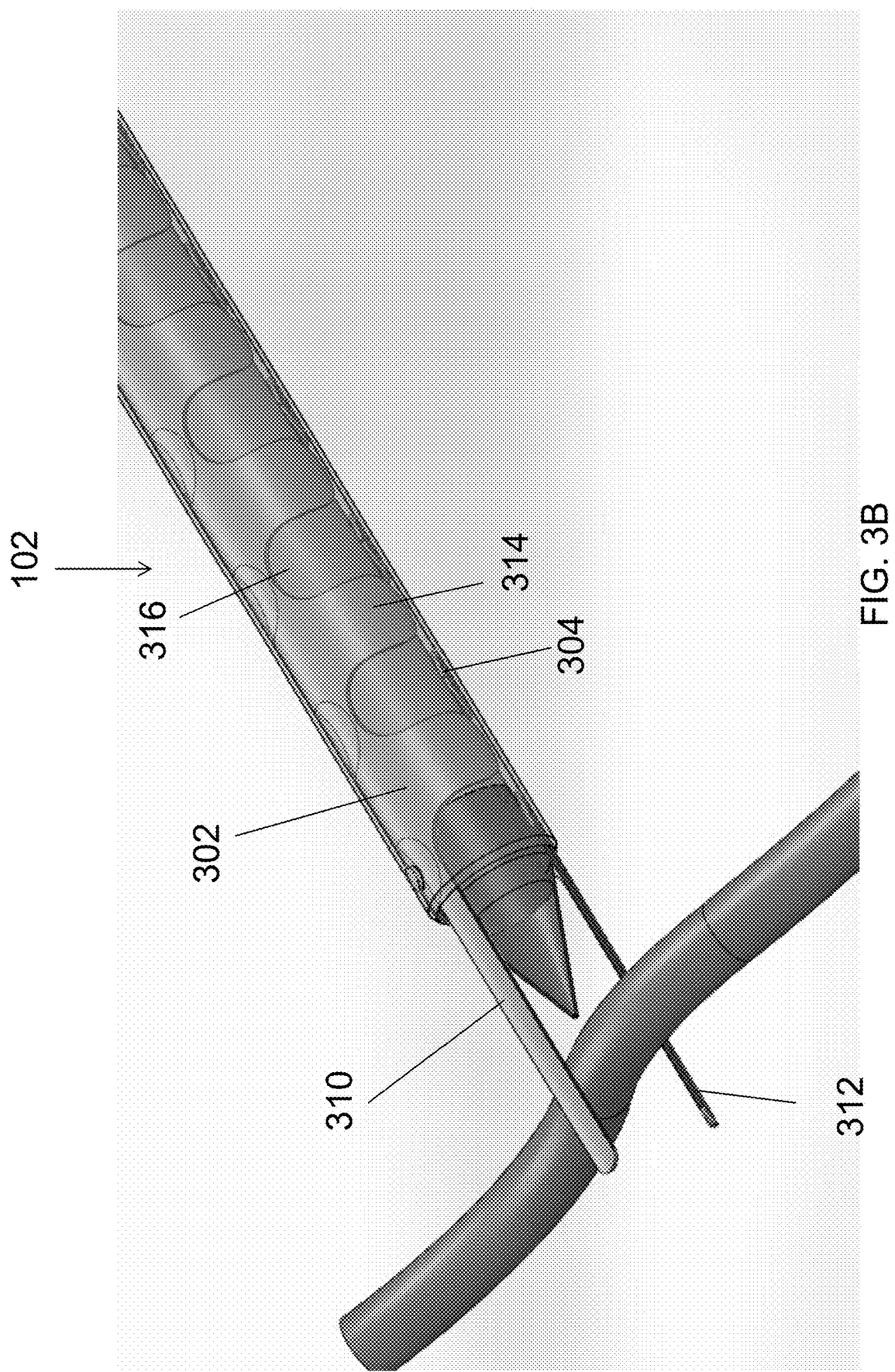
Figure 3C:
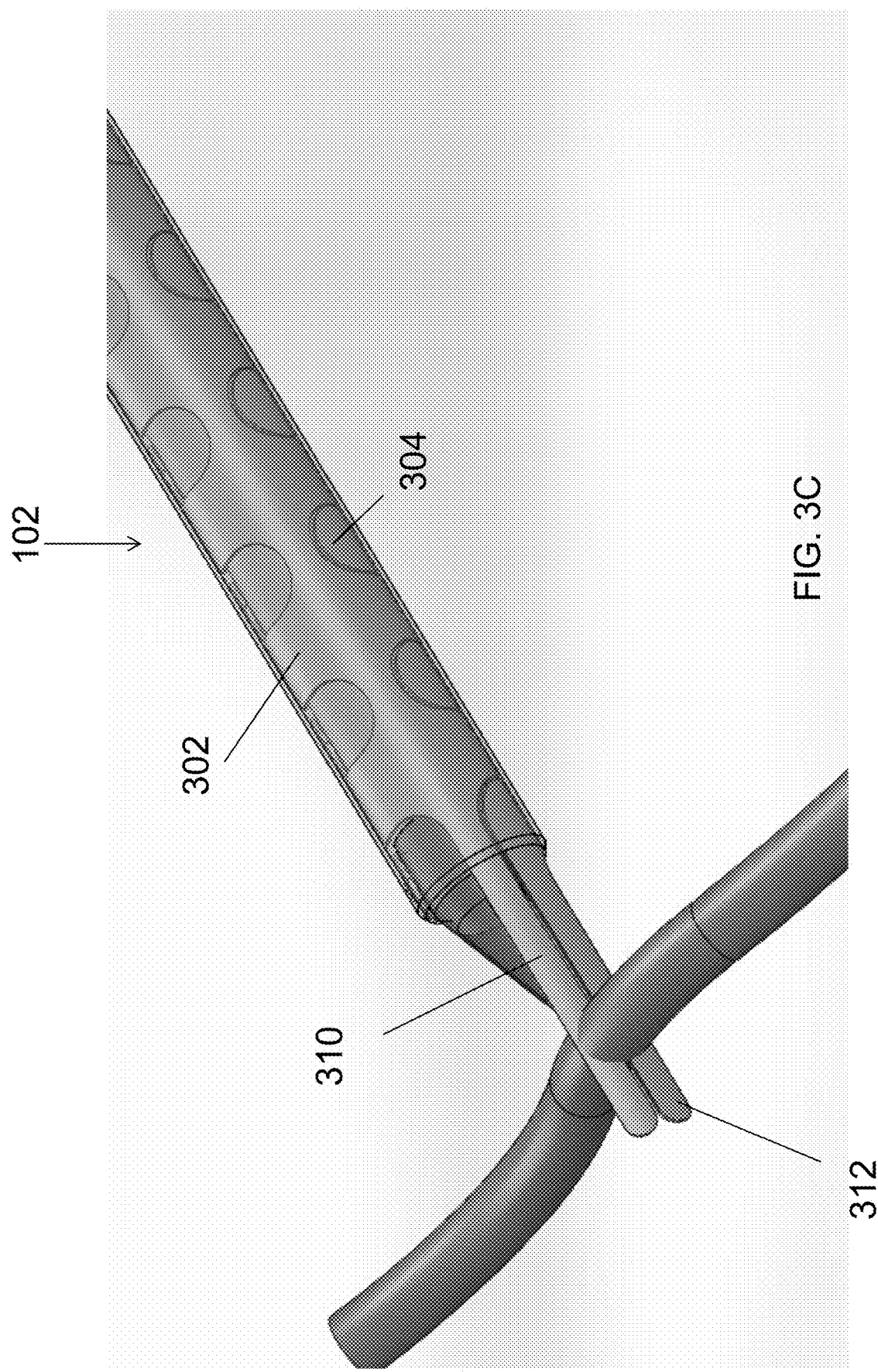

The first cutting member 302 and the second cutting member 304 may be moveable in a longitudinal direction relative to the elongated body 102 of the cannula 100. In this manner, the cutting portions 310, 312 may be moved from an initial, retracted position during the dissection, in which the cutting portions 310, 312 are retracted substantially proximally of the dissection tip 120 not to interfere with the dissection, to an operational or extended position for sealing and cutting, in which the cutting portions 310, 312 may be advanced distally for the user to see the cutting portions and to provide enough capture length for the vessel. In some embodiments, the cutting portions 310, 312 may at least partially extend beyond the dissection tip 120 to capture a blood vessel the cutting portions 310, 312. In addition, in some embodiments, the first cutting member 302 and the second cutting member 304 may be rotatable relative to one another. In this manner, the cutting portions 310, 312 may be moved from an open position when the cutting portions 310, 312 are apart or spaced away from one another to capture a blood vessel therebetween, as shown in FIG. 3B, to a closed position when the cutting portions 310, 312 are brought towards one another around the dissection tip 120 to seal and cut the blood vessel, as shown in FIG. 3C. In some embodiments, the first cutting member 302 and the second cutting member 304 are configured so both cutting portions 310, 312 can be rotated circumferentially about the dissection tip 120 toward one another in both clockwise and counterclockwise direction depending on the location of the blood vessel to be captured between the cutting portions 310, 312. Such bi-directional, circumferential movement of the cutting portions 310, 312 may allow the user to operate on blood vessels on all sides of the cannula 100 to save time and reduce cannula manipulation during the procedure as the user does not need to be concerned about the orientation and position of the cannula 100 in relation to the blood vessel. In addition, it may reduce the potential for the cutting portions to twist the side branches, thereby exerting traction on the blood vessel and consequent damage to the graft. The bi-directional movement may also be more-intuitive to the user and eliminates the need to remember which side is the active side for cautery and cutting. In other embodiments, one of the cutting portions 310, 312 may be stationary and the other one may rotate in both clockwise and counter-clockwise toward the stationary cutting portion for easier manipulation and visualization of the cutting portions 310, 312. Of course, the stationary cutting portion may also be moved to a desired orientation by moving the cannula 100.

The cutting portions of the cutting members 302, 304 may generally be elliptical or blade-like with a rounded distal tip, but any other shape that enables the cutting and sealing of a blood vessel may also be used. To facilitate sealing of the blood vessel, one or both of the cutting portions 310, 312 may be energized, when needed, using various sources of energy, including, but not limited to, resistive heating, ultrasound heating, and bipolar or monopolar RF energy. In some embodiments, the electrodes can be controlled independently of one another. In some embodiments, the cutting portions 310, 312 may be made from a material such as metal that would enable the cutting portions 310, 312 themselves to be energized. Additionally or alternatively, energizing elements, such as metal wires, may be disposed on the cutting portions 310, 312. When energized, the energizing elements may be brought in contact with the blood vessel by the cutting portions 310, 312 to seal the blood vessel. In some embodiments, one or both of the cutting members 310, 312 may include protrusions for use as spot cautery. In some embodiments, one or both of the cutting members 310, 312 may have a sharpened, thin edge for concentrated application of energy to the blood vessel. Such concentrated energy application may require less energy to be applied to the side branch, thereby minimizing extension of cauterizing energy from the side branch towards the main trunk of the blood vessel, and thus eliminating potential trauma to the blood vessel.

To facilitate cutting of the blood vessel subsequent to sealing of the blood vessel, in some embodiments, one of the opposing edges 318, 320 of the cutting portions 310, 312 between which cutting occurs may have a leveled face while the other one may be a sharpened, thin or pointed so that the tissue is not cut in a scissor-like motion but with a thin edge against a flat surface. To that end, in some embodiments, both edges of the cutting members 310 may be sharpened edges, while both edges of the cutting portion 312 may be flat, or vise versa. Alternatively, the cutting portions 310, 312 may have one sharp edge or blade edge and one flat edge with the sharp edge of one cutting portion facing the flat edge of the other cutting portion. It should be noted that in some embodiments, the blood vessel may be both sealed and cut using energy, as described above. It should of course be understood that, in some embodiments, the opposing edges the opposing edges 318, 320 of the cutting portions 310, 312 may both be sharpened so the tissue is cut in a scissor-like manner.

As shown in FIG. 3B and FIG. 3C, in some embodiments, the cutting members 302, 304 may be substantially u-shaped and disposed in the same plane relative to the cannula body 102. In some embodiments, the cutting members 302, 304 may include respective cutouts and fingers 314, 316 along the edges to enable circumferential movement of the cutting members 302, 304 relative to one another.

Figure 4B:
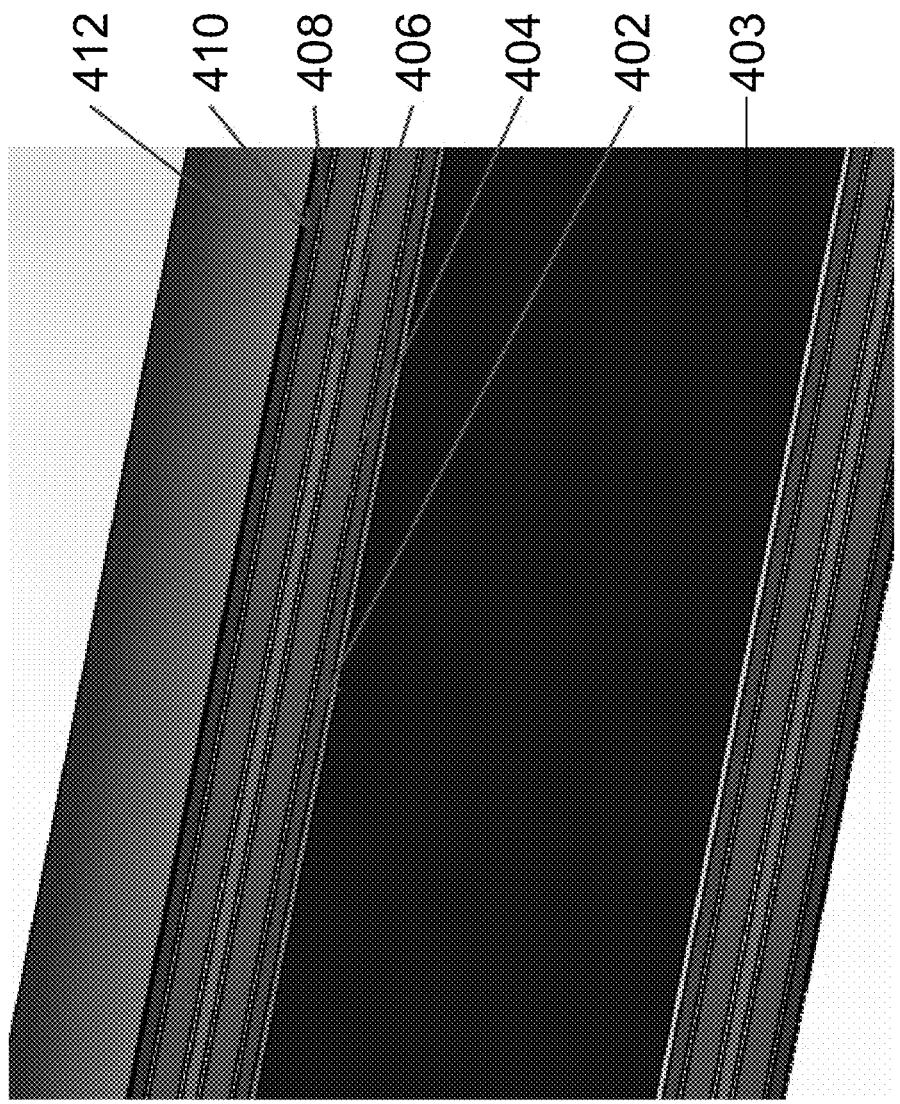

In reference to FIG. 4A and FIG. 4B, in some embodiments, the cutting members 302, 304 may be substantially tubular and be disposed in different planes of the cannula body 102. As shown in FIG. 4A, in some embodiments, the cutting member 304 may be concentrically disposed inside within the cutting member 302. Referring to FIG. 4B, in some embodiments, the elongated body 102 of the cannula 100 may be constructed of a series of coaxial tubes, both metal and plastic, that may act as the structural main shaft, the electrical conductive and insulative paths, and the end-effectors, i.e. cutting portions 310, 312. In some embodiments, there may be three plastic sheaths acting as electrical insulators and mechanical bearing surfaces sandwiched in between two metal conductive tubes for the entire length of the device. The innermost layer may be the inner sheath 402 (plastic) defining an internal lumen 403. The inner sheath 402 may be followed outwardly by the inner electrode tube 404 (metal), middle sheath 406 (plastic), outer electrode tube 408 (metal) and outer sheath 410 (plastic), and finally a shrink jacket 412. In some embodiments, instead of three plastic sheaths, the electrical insulation may be provided using non-conductive coatings or similar means. For example, in some embodiments, the electrodes 404, 408 may be coated with polyvinyldyne flouride (PVDF), but other non-conductive coating may also be used.

The inner electrode tube 404 and the outer electrode tube 408 may be used to form the first cutting member 302 and the second cutting member 304, with the cutting portions 310, 312 being formed at the distal ends of the inner electrode tube 404 and the outer electrode tube 408. To enable the cutting portions 310, 312 to capture, seal and cut blood vessels, the inner electrode tube 404 and the outer electrode tube 408 may be slidable in the longitudinal direction relative to the cannula 100 and rotatable relative to one another. Further, because the cutting portions 310, 312 are formed from the inner electrode tube 404 and the outer electrode tube 408, the cutting portions 310, 312 can be easily energized through the inner electrode 404 and the outer electrode 408. In some embodiments, the cutting portion formed from the inner electrode tube 404 (i.e. inner cutting portion 411) may be bent out of the plane of the inner electrode 404 to enable it to rotate along the same axis and be co-radial with the cutting portion formed in the outer electrode 408 (i.e. outer cutting portion 413). In some embodiments, the inner cutting portion 411 may have a flat face 416 on either side of the inner cutting portion, while the outer cutting portion 413 may have a sharpened or blade edge 418 on both sides, or vice versa. In other embodiments, as described above, each cutting portion 411, 413 may have one sharpened edge and one flat edge, with the flat edge of one cutting portion facing the sharpened edge of the other cutting portion.

Figure 4C:
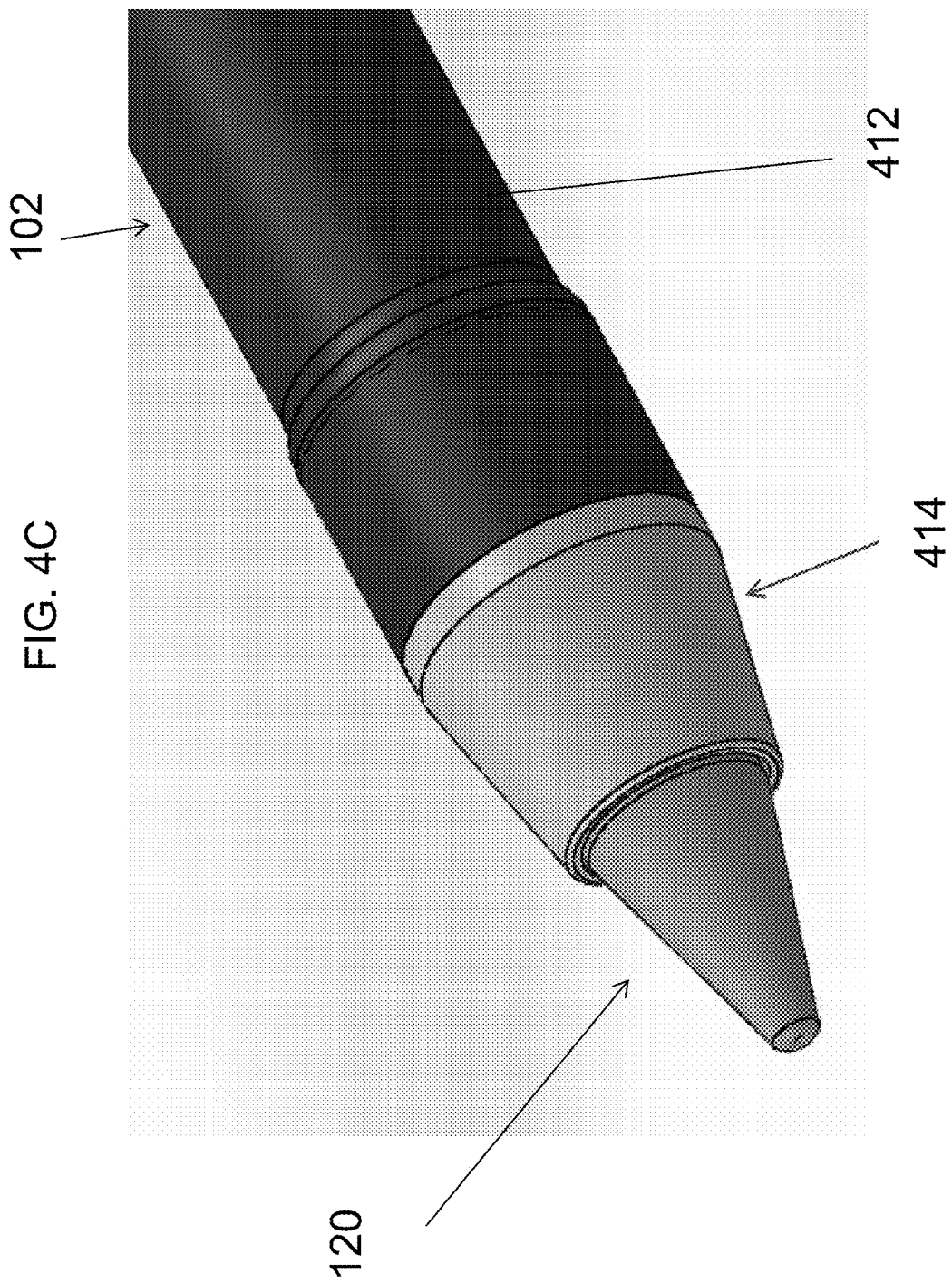
Figure 4D:
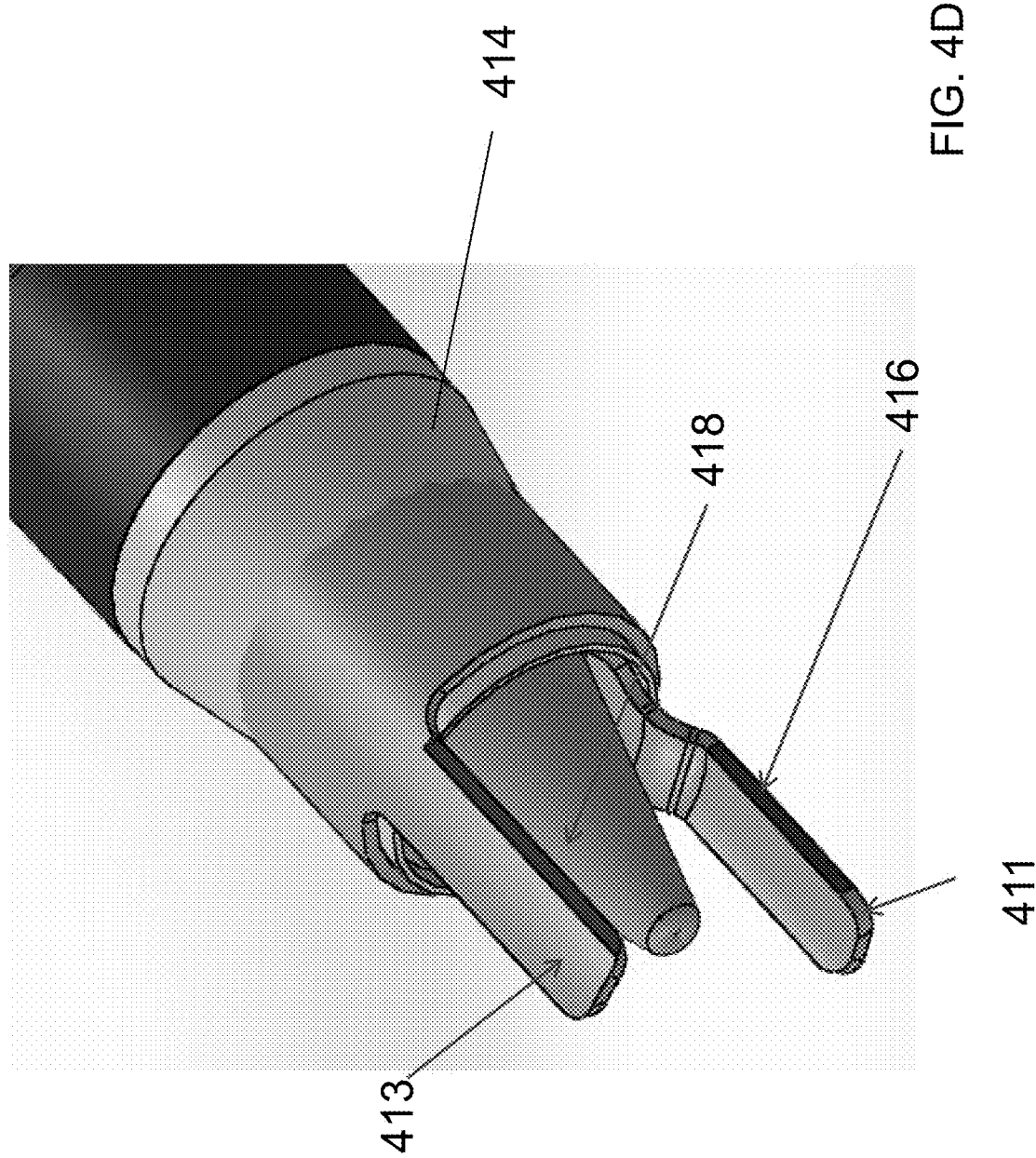

In reference to FIG. 4C, in some embodiments, the dissection tip 120 may be connected to the inner sheath 402 to enable the advancement of the endoscope 116 into the dissection tip though the internal lumen 403. A sleeve 414, or transition, may be used to protect tissue from damage during dissection by smoothing the geometry between the dissection tip 120 and the cannula body 102. The distal end of the sleeve 414 may be left unattached to the dissection tip 120 to allow the cutting portions 312, 314 to be advanced distally through the sleeve 414, as shown in FIG. 4D. In some embodiments, the sleeve 414 may be made of a flexible material so during dissection the sleeve 414 would comply with the dissection tip creating a smooth transition and also a tight seal to prevent tissue or bodily fluids from entering the cannula 100. On the other hand, a flexible sleeve would be able to deflect and expand to allow the cutting portions 312, 314 to be advanced out distally though the sleeve 414. In some embodiments, the surface of the sleeve may be coated with a lubricious substance to make the extension of the cutting portions 312, 314 through the sleeve 414 easier and smoother by decreasing friction between the cutting portions 312, 314 and the sleeve 414. The thin-walled shrink tube 412 may be placed over the outer surface of the cannula body for aesthetic purposes and to assist in securing the transition.

Figure 5:
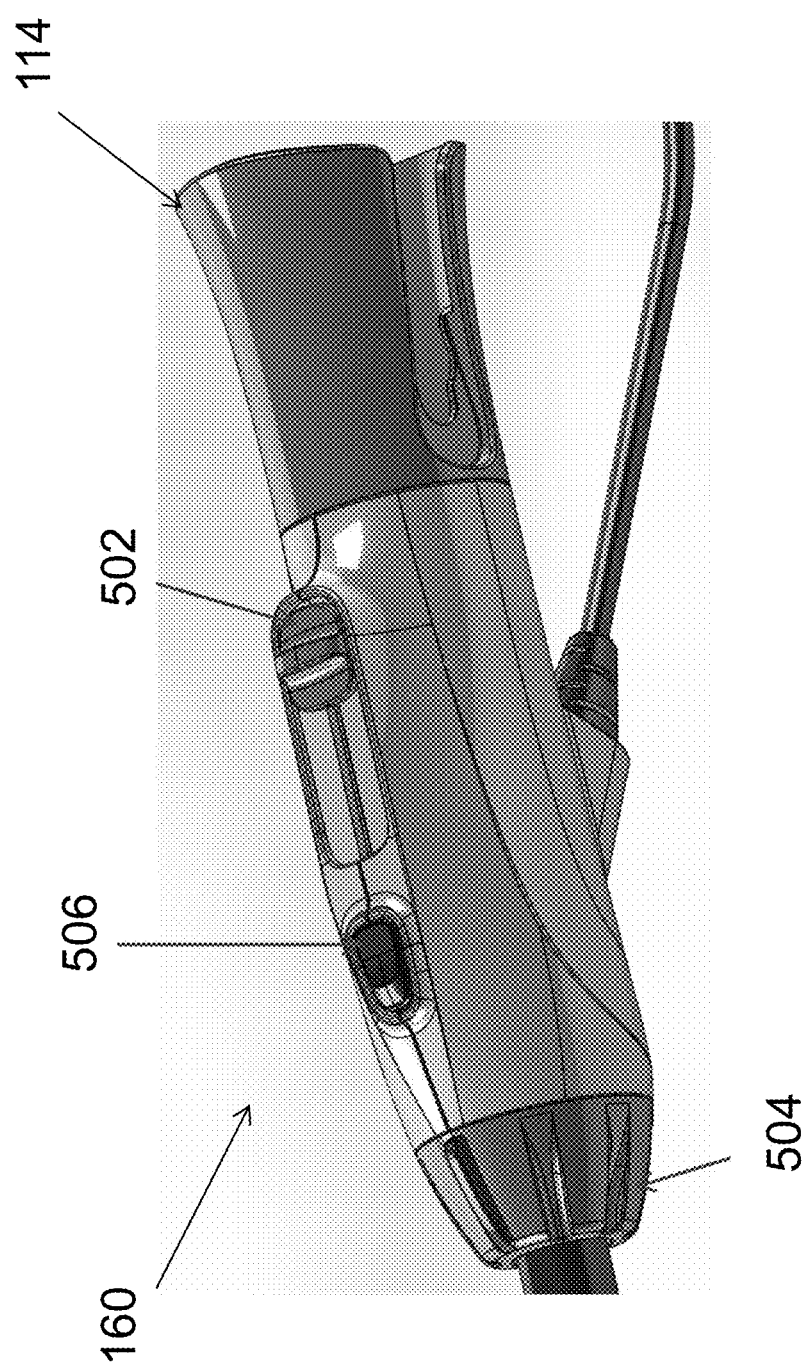
FIG. 5 illustrates an embodiment of a control handle suitable for use with an endoscopic cannula of the present disclosure.

FIG. 5 illustrates an embodiment of the control handle 160 for controlling the cutting members 310, 312. In some embodiments, the control handle 160 may include a translation control 502 for advancing and retracting the cutting members 310, 312. The control handle further includes a rotation control 504 for rotating the cutting members with respect to one another. Finally, the control handle 160 includes an energy control 506 for supplying energy (such as bipolar RF energy) to the cutting portions 310, 312. The adapter 114 may be located at the proximal end of the control handle 160 for advancing the endoscope 116 into the endoscopic cannula 100.

In operation, an initial incision may be made in conventional manner to expose the target vessel (e.g., the saphenous vein). The cannula 100 may be inserted into the incision and guided to the target vessel. In some embodiments, the cannula 100 may include a smooth tubular sheath around the elongated body 102 for sealing the cannula 102 within the port through which the cannula 102 is introduced into the patient. The cannula 100 may then be advanced substantially along the target vessel to dissect the target vessel from the surrounding tissue. In some embodiments, the cannula 100 may be introduced through a sealable port used to seal the incision to allow insufflation of the space created by the dissection of the target vessel from surrounding tissues.

As the cannula 100 is being advanced, the cutting portions 310, 312 of the cutting elements 302, 304 may be kept in a retracted position so not to interfere with tissue dissection until a branch vessel is encountered. At that point, the cutting portions 310, 312 may be advanced beyond the dissection tip 120, as described above, to capture, seal and cut the branch vessel.

In reference to FIGS. 6A-6F, in some embodiments using the control handle 160, the cutting portions 310, 312 may be moved from a retracted position, as shown in FIGS. 6A-6B, in the distal direction beyond the dissection tip 120 by advancing the translational control 504 on the handle to its distal position, as shown in FIGS. 6C-6D. The cutting portions 310, 312 may be advanced out together and enter into the field of view of the endoscope in the dissection tip 120. Next, the cutting portions 310, 312 may be rotated with respect to one another using the rotation control 504, as shown in FIGS. 6E-6F, for sealing and cutting the branch vessel. The cutting portions 310, 312 may be rotated around the dissection tip 120 in a circular arc motion. The endoscopic cannula 100 may be positioned such that the target branch vessel may lay across one of the cutting portions 310, 312, regardless of orientation of the branch vessel in relation to the main blood vessel to be harvested. The endoscopic cannula 100 may be designed such that the user can place the endoscopic cannula 100 and the cutting portions 310, 312 as far away from the target main vessel as possible to avoid injury to the main vessel. Once in position, the user may rotate one of the cutting portions 310, 312 toward the other one until the branch vessel is captured. If positioned properly, the rotation is preferably always away from the main vessel, thus increasing and further maximizing the potential negative effects of lateral thermal spread. Next, when the branch vessel is positioned in between the cutting portions 310, 312, the user may depresses the energy control 508 button to transfer the energy into the tributary to seal the vessel. After sealing is complete and the energy control button 508 is released, the user may continue to advance the rotation control 504 until the cutting portions 310, 312 transect the branch vessel. The user may then retract the cutting portions 312, 314 with the translation control 502 and advance the device to the next branch vessel until all tributaries have been successfully ligated and transected.

After the branch vessel has been hemostatically severed, the cannula 100 may be advanced forward until the next branch vessel is encountered, at which point the branch vessel may be sealed and severed using the cutting unit 300. Once all branch vessels along a desired length of the target vessel have been sealed and severed, the cannula 100 may be used to seal and cut the target vessel according to procedure similar to the procedure used to cut and seal the branch vessels. Alternatively, the cannula 100 may be withdrawn, and another surgical device may be used to seal and cut the main vessel.

In some embodiments, the cannula 100 of the present disclosure may allow vessel sealing and cutting to be performed in a small cavity. Accordingly, when using the cannula 100 of the present disclosure there may not be a need to maintain the perivascular cavity in an expanded state and thus the procedure may be performed without gas insufflation of the perivascular cavity. In operation, the transparent dissection tip 120 can deflect a vessel to one side, so that the members of the cutting unit can capture the vessel, while maintaining visualization of all components in a collapsed tissue tunnel. Vessel harvesting in a small or collapsed cavity may be useful in anatomic situations characterized by vessel tortuosity, such as the internal mammary artery and vein. Harvesting without gas insufflation may also be beneficial to the graft. The carbonic acid environment of a cavity maintained by carbon dioxide gas insufflation may be detrimental to the graft vessel. A lower pH atmosphere surrounding the vessel may alter the cellular viability of the graft, potentially leading to early graft failure. Positive pressure produced by gas insufflation may also collapse the vessel, causing hemostasis, and may increase the potential for intraluminal clot formation. Presence of intraluminal clot may cause graft thrombosis and early graft failure.

Figure 7A:
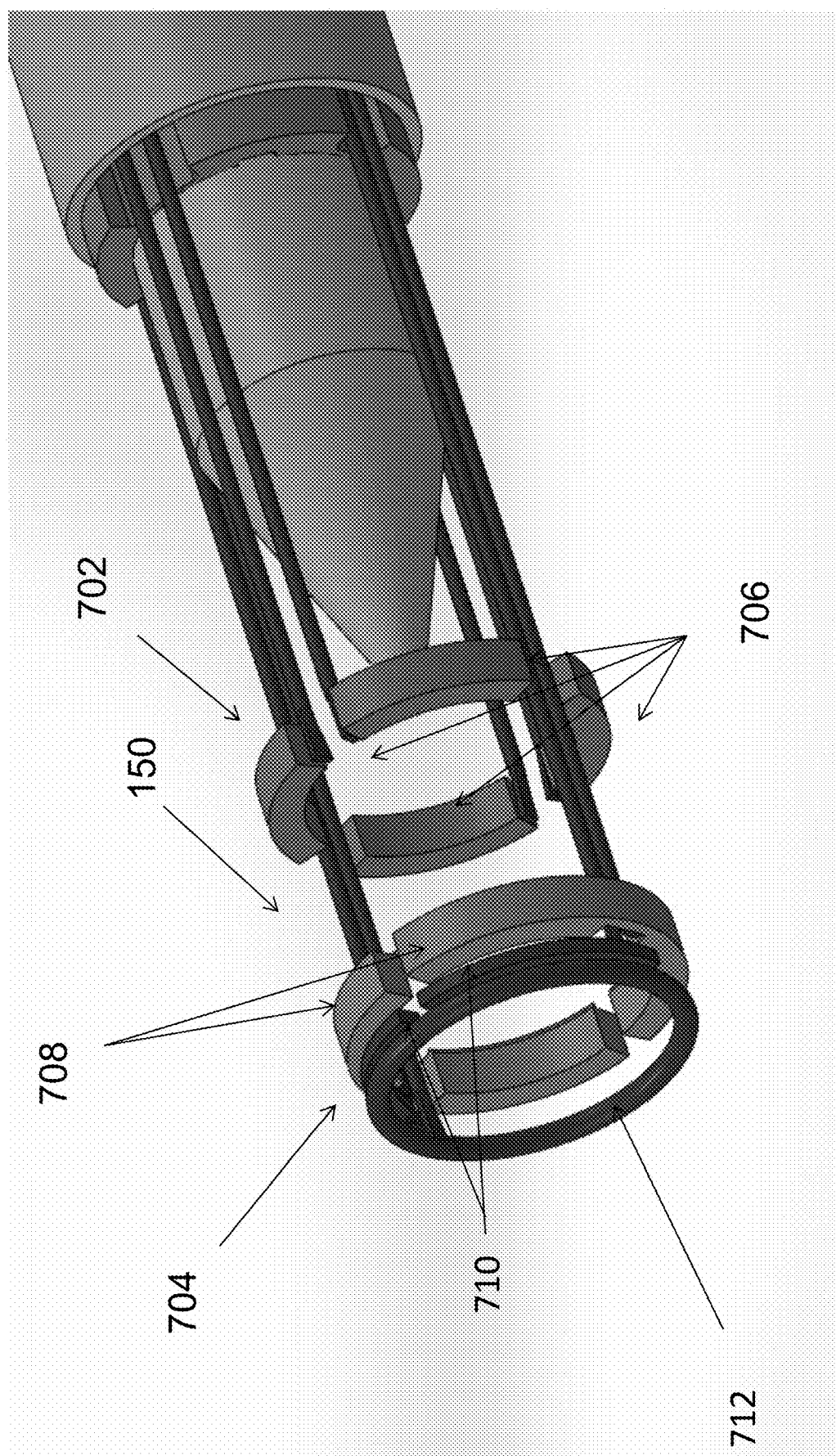

In reference to FIG. 7A and FIG. 7B, the cutting unit 150 may include a first member 702 and a second member 704. In some embodiments, the first member 702 and second member 704 may be translatable relative to the dissection tip 120 from a proximal position, during the dissection, to a more distal position to capture, seal and cut the blood vessel. Moreover, the first member 702 and second member 704 may also be moveable relative to one another so the first member 702 and second member 704 can be space away from one another capture a blood vessel therebetween and then may be compressed against one another to seal and cut the blood vessel. To permit such movements of the first member 702 and second member 704, in some embodiments, the first member 702 and second member 704 may be mounted on one or more actuating rods for advancing and retracting. It should, of course, be understood that other mechanisms for translating the first member 702 and second member 704 relative to the dissection tip 120 and one another may be employed.

The first member 702 may include four circumferentially-disposed proximal electrode segments 706 for bipolar RF cutting. The proximal electrode segments may be connected by 0.020" conductor. The second member 704 may include two circumferentially-disposed distal electrode segments 708 for bipolar RF cutting. The distal electrode segments may be connected by 0.020" conductor. In addition, the second member 704 may include two segments 710 for resistive heat cautery 706 disposed distally of the distal electrode segments, and a distal ring electrode 712 for monopolar cautery. The actuating rods may be employed to energize the electrodes 706-712.

Figure 8:
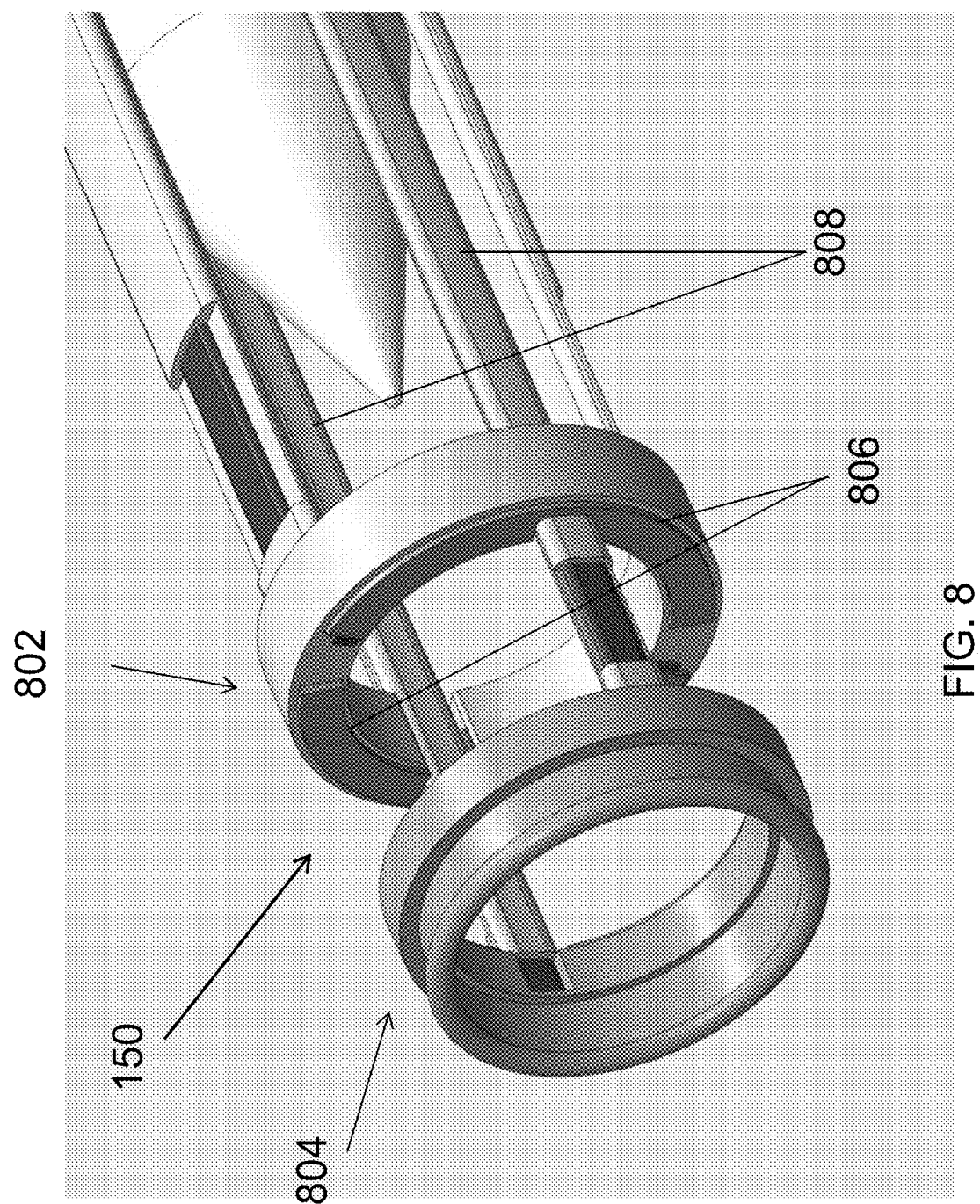
FIG. 8 illustrates an embodiment of a cutting unit of an endoscopic cannula of the present disclosure.

In reference to FIG. 8, in some embodiments, the cutting unit 150 may include a first member 802 and a second member 804. The first member 802 and the second member 804 are translatable relative to the dissection tip and one another, as described above. In this embodiment of the cutting unit 150, the three electrodes 708, 710, and 712 of the second member 704 (see FIGS. 7A and 7B) are combined into one solid ring. In bipolar mode the only one side of the ring may work with active proximal segment. In monopolar mode, the entire ring may work with outside returned electrode. In some embodiments, two large cross-section conductors may also replace four electrode segments, two for RF cutting and two for resistive heat cautery, which may increase rigidity of the distal structure.

Moreover, the four electrodes 706 of the first member 702 can also be combined into two hemispheric electrodes 806, which can be individually controlled. In this manner, only two larger cross-section conductors 808 may be used instead of four small ones, as in the cutting unit illustrated in FIGS. 7A and 7B. Rigidity of the proximal structure may also increase by combining the four electrodes into two.

Figure 9A:
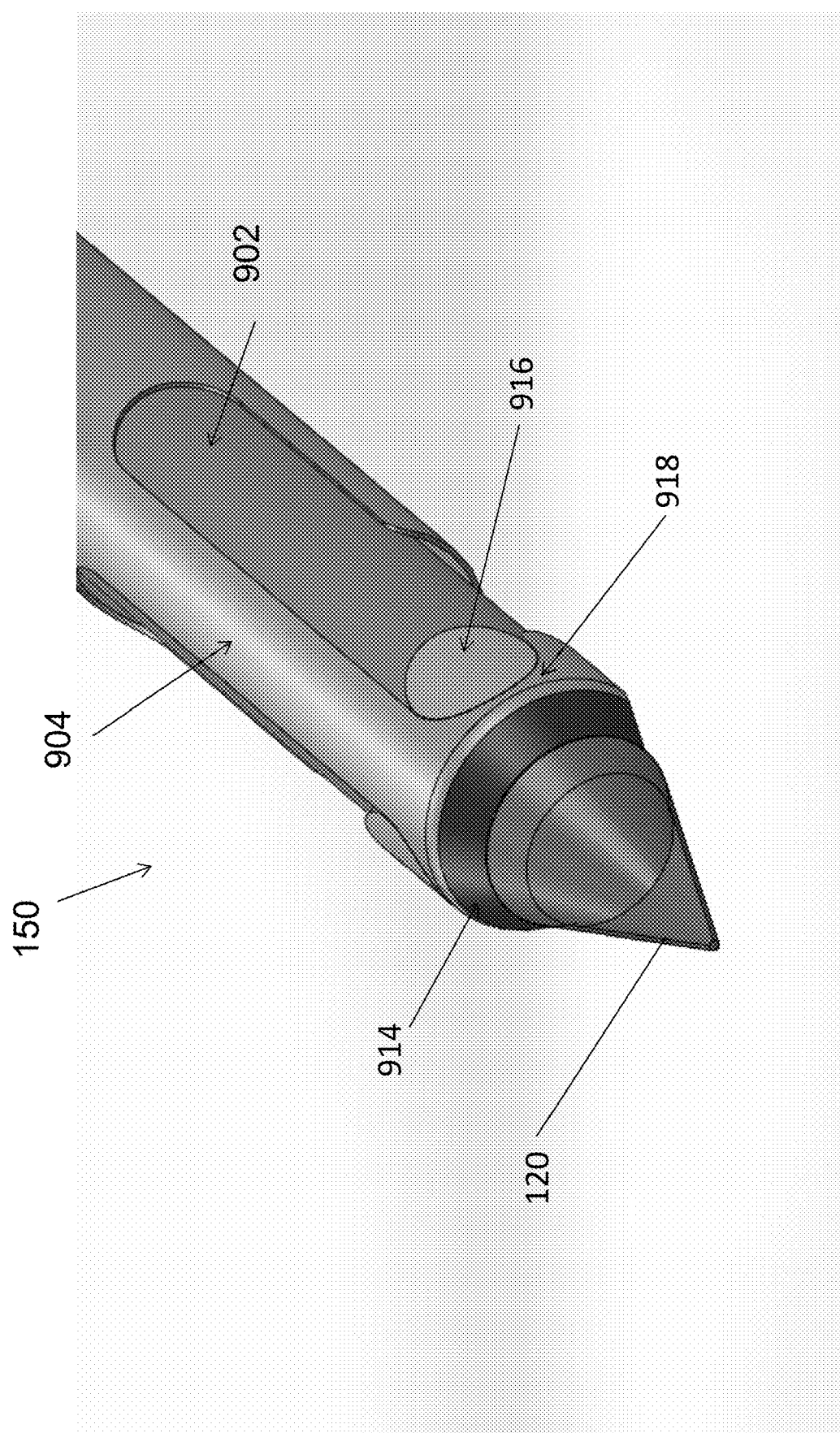
FIG. 9A, FIG. 9B and FIG. 9C illustrate an embodiment of a cutting unit of an endoscopic cannula of the present disclosure.

In reference to FIG. 9A, in some embodiments, the cutting unit 150 may include a first member 902 having a proximal electrode 916 for bipolar RF cutting. The cutting unit 150 may also include a second member 904 having a distal electrode 918 for bipolar RF cutting. The cutting unit 150 may further include an electrode 914 for monopolar spot cautery disposed over the dissection tip 120. In some embodiments, the first member 902 and the second member 904 may be made of a conductive material, with optional coating, and the electrodes 914, 916, 918 may be energized through the cutting member 902, 904.

Figure 9B:
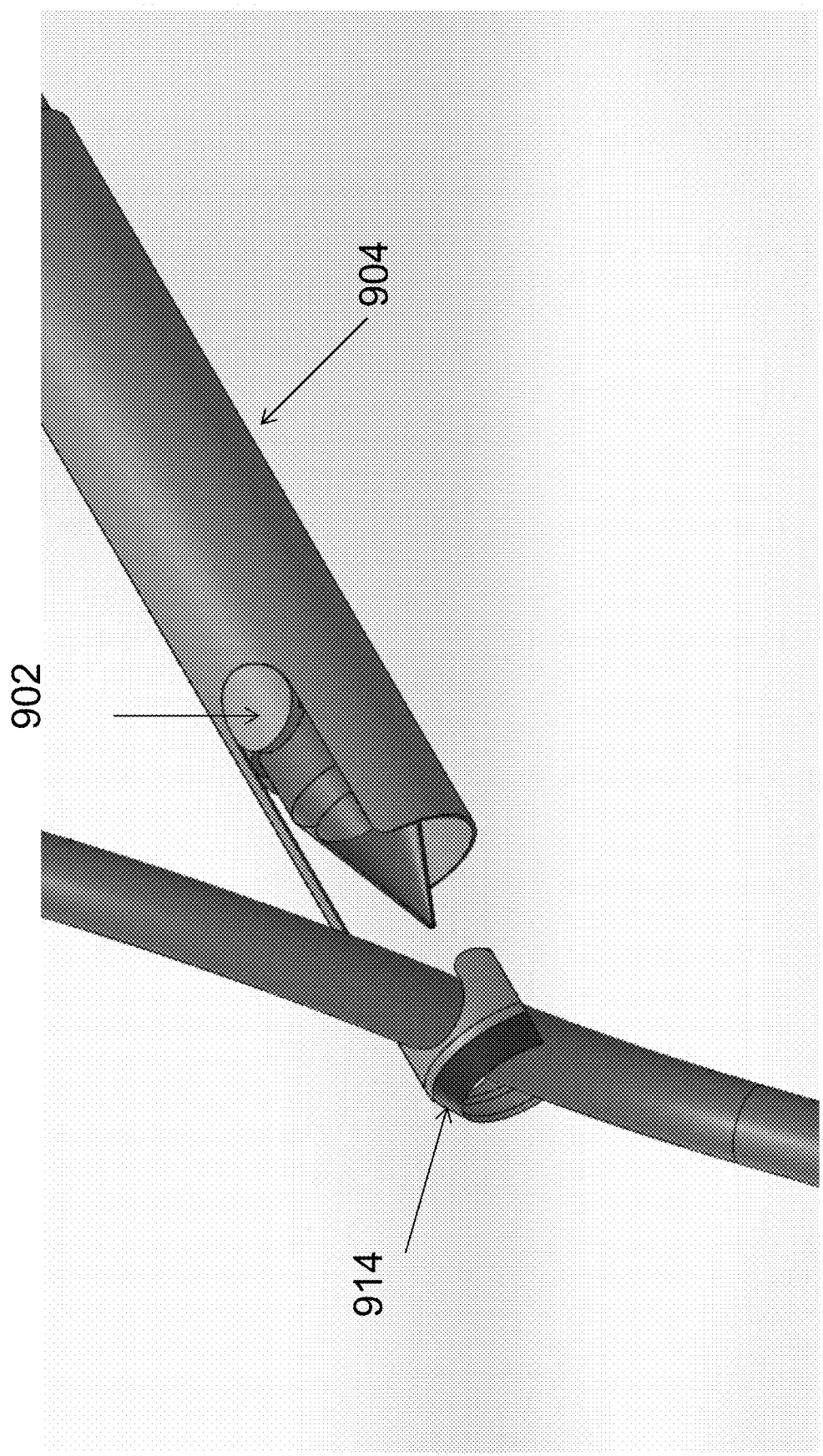
Figure 9C:
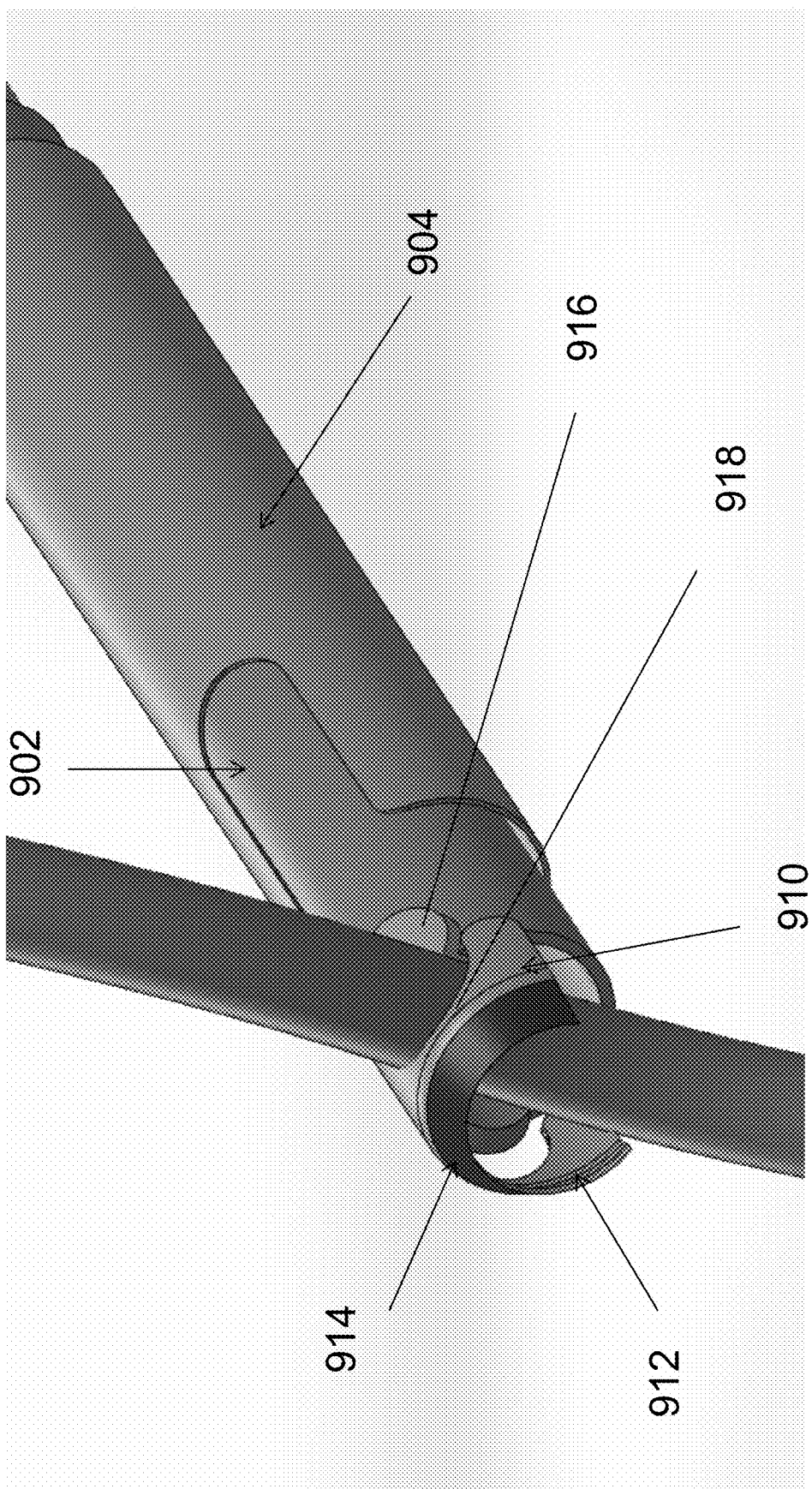

In reference to FIG. 9B and FIG. 9C, in some embodiments, the first member 902 and the second member 904 may be tubular, with the first member 902 slidably disposed relative to the second member 904 to enable the first member 902 and the second member 904 to be biased relative to one another in a longitudinal direction. In some embodiments, the first member 902 and the second member 904 may be move in a distal direction between an inactive position proximal of the dissection tip 120, as shown in FIG. 9A, and an active position in the field of view of the endoscope, as shown in FIG. 9B and FIG. 9C, for capturing, cutting and sealing the blood vessel.

The second member 904 may include one or more hooks 910, 912 at a distal region of the second member 904. The hooks 910, 912 may be configured to capture the branch vessel, as shown in FIG. 9B. In some embodiments, the second member 904 may include two hooks 910 and 912, in a spaced relation to one another, so that the branch vessel may be contacted, at a minimum, by one of the hooks.

In operation, the cannula 100 may be advanced to a vessel with the first member 902 and the second member 904 of the cutting unit 150 positioned proximally to the dissection tip 120. As the vessel is encountered, as shown in FIG. 9B, first, the second member 904 may be extended in the distal direction to capture the branch vessel by the hook of the second member 904. Spot cautery may also be performed in this position, as desired, by a spot cautery electrode 914. Next, the first member 902 may be advanced to pinch the branch vessel between the electrodes 916, 918 of the first member 902 and the second member 904, and the RF current may be turned on for sealing and cutting the branch vessel captured in the cutting unit 150.

FIG. 10A and FIG. 10B illustrate yet another embodiment of the cutting unit 150 having a first member 1002 and a second member 1004. In comparison to the embodiment of the cutting unit shown in FIGS. 9A-9C, the second member 1004 may include only a single hook 1010 on one side of the second member 1004, as compared to two hooks 910, 912 on the second member 904. Removing one of hooks may improve visualization of the procedure by the endoscope 116 disposed within the cannula 100. Otherwise, the structure and operations of this embodiment of the cutting unit 150 may similar to those of the embodiment of the cutting unit 150 disclosed in FIGS. 9A-9C.

It should be noted while preferred types of energy for various electrodes are indicated in the present disclosure, all electrodes can be energized using various sources of energy, including, but not limited to, resistive heating, ultrasound heating, and bipolar or monopolar RF energy. In some embodiments, the electrodes can be controlled independently of one another. It should also be noted that, when appropriate, the electrodes may be insulated with an insulating coating or insulating sheath.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A surgical device comprising:
an elongated body having a proximal end and a distal end;
a conical tip that has an inner cavity for receiving an endoscope and disposed at the distal end of the elongated body, the conical tip having a shape that minimizes tissue trauma during dissection and having on its surface a coating to further reduce friction during dissection and to provide resistance to fluids and tissue to remain on the coated surface of the conical tip;
one or more lumens in fluid communication with an inner cavity of the conical tip and into which an endoscope can be advanced into the inner cavity for endoscopic viewing of a harvesting procedure performed by the surgical device; and
a cutting unit having a first cutting portion and a second cutting portion, the first cutting portion and the second cutting portion being moveable in a longitudinal direction relative to the elongated body to capture a blood vessel between the first cutting portion and the second cutting portion and being rotatable relative to one another circumferentially about the conical tip to cut the captured blood vessel.

2. The device of claim 1, wherein the coating on the coated surface of the conical tip provides increased lubricity of the conical tip.

3. The device of claim 2, wherein the coating may be selected from one of paralene, polytetrafluoroethylene, fluorinated ethylene propylene, silicon or tethered liquid perfluorocarbon.

4. The device of claim 2, wherein the conical tip further comprises a conditioned conical tip, the conditioned conical tip having at least one conditioned surface having increased optical clarity.

5. The device of claim 2, wherein the conical tip further comprises an inflatable tip, the inflatable tip having an inner cavity in communication with one or more lumens and into which an endoscope is advanced for endoscopic viewing of a harvesting procedure performed by the surgical device.

6. The device of claim 1, wherein the first cutting portion and the second cutting portion are moveable in the longitudinal direction relative to the elongated body from a first position proximal of the conical tip to a second position in a distal direction beyond the conical tip and being rotatable circumferentially about the conical tip.

7. The device of claim 1, wherein the coating is applied in thin layers amounting to less than 0.001" in thickness.

8. The device of claim 1, wherein the coating on the conical tip will resist fluids and tissue from remaining on the coated surface and provide for reduced dissection loads by reducing friction during the procedure.

9. The device of claim 1, wherein the coating is one of a hydrophobic and oleophobic material.

10. A surgical device comprising:
an elongated body having a proximal end and a distal end;
an inflatable tip disposed at the distal end of the elongated body, the inflatable tip having a shape that minimizes tissue trauma during dissection and having on its surface a coating to further reduce friction during dissection and to provide resistance to fluids and tissue to remain on the coated surface of the inflatable tip, the inflatable tip having an inner cavity in communication with one or more lumens and into which an endoscope is advanced for endoscopic viewing of a harvesting procedure performed by the surgical device;
a cutting unit having a first cutting portion and a second cutting portion, the first cutting portion and the second cutting portion being moveable in a longitudinal direction relative to the elongated body to capture a blood vessel between the first cutting portion and the second cutting portion and being rotatable relative to one another circumferentially about the inflatable tip to cut the captured blood vessel.

11. A surgical device comprising:
an elongated body having a proximal end and a distal end;
an inflatable tip disposed at the distal end of the elongated body, the inflatable tip having a shape that minimizes tissue trauma during dissection and having on its surface a coating that improves optical clarity through the inflatable tip and further reduces friction during dissection and to provide resistance to fluids and tissue to remain on the coated surface of the inflatable tip; and
a cutting unit having a first cutting portion and a second cutting portion, the first cutting portion and the second cutting portion being moveable in a longitudinal direction relative to the elongated body to capture a blood vessel between the first cutting portion and the second cutting portion and being rotatable relative to one another circumferentially about the inflatable tip to cut the captured blood vessel.

\* \* \* \* \*